US011147536B2

(12) United States Patent
Mauldin, Jr. et al.

(10) Patent No.: US 11,147,536 B2
(45) Date of Patent: Oct. 19, 2021

(54) LOCALIZATION OF IMAGING TARGET REGIONS AND ASSOCIATED SYSTEMS, DEVICES AND METHODS

(71) Applicant: Rivanna Medical LLC, Charlottesville, VA (US)

(72) Inventors: Frank William Mauldin, Jr., Charlottesville, VA (US); Kevin Owen, Crozet, VA (US); Adam Dixon, Charlottesville, VA (US)

(73) Assignee: Rivanna Medical LLC, Charlottesville, VA (US)

( * ) Notice: Subject to any disclaimer, the term of this patent is extended or adjusted under 35 U.S.C. 154(b) by 494 days.

(21) Appl. No.: 15/866,638

(22) Filed: Jan. 10, 2018

(65) Prior Publication Data

US 2018/0153513 A1    Jun. 7, 2018

Related U.S. Application Data

(63) Continuation-in-part of application No. 14/770,896, filed as application No. PCT/US2013/077917 on Dec. 27, 2013.

(Continued)

(51) Int. Cl.
*A61B 8/00* (2006.01)
*G06F 1/16* (2006.01)
(Continued)

(52) U.S. Cl.
CPC ............... *A61B 8/462* (2013.01); *A61B 8/44* (2013.01); *A61B 8/4427* (2013.01); *A61B 8/463* (2013.01);
(Continued)

(58) Field of Classification Search
CPC ......... A61B 8/462; A61B 8/4427; A61B 8/44; A61B 8/54; A61B 8/467; A61B 8/463;
(Continued)

(56) References Cited

U.S. PATENT DOCUMENTS 4,476,873 A   10/1984   Sorenson et al.
4,913,157 A   4/1990    Pratt, Jr. et al.
(Continued)

FOREIGN PATENT DOCUMENTS

CN   1042778    6/1990
CN   1968655    5/2007
(Continued)

OTHER PUBLICATIONS

P. Foroughi et al., "Ultrasound Bone Segmentation Using Dynamic Programming", IEEE Ultrasonics Symposium, 2007, p. 2523-2526.
(Continued)

*Primary Examiner* — Sean D Mattson
(74) *Attorney, Agent, or Firm* — Woods Rogers PLC; Nathan A. Evans

(57) ABSTRACT

Handheld ultrasound imaging devices for identification of target regions are generally described. Medical ultrasound is a popular medical imaging modality primarily used for diagnostic imaging of soft tissue but also for interventional procedures such as guidance of a needle or catheter placement. Examples include diagnostic imaging of organs, such cardiac or liver structures. Common interventional procedures that rely on ultrasound guidance are central line placement and guidance of nerve blocks, both of which are high volume procedures in certain hospital settings such as the intensive care unit (ICU). Handheld ultrasound imaging devices with integral display screens and improve portability are described, along with systems and methods for orienting (Continued)

displayed ultrasound images so as to improve their usefulness in guiding interventional procedures.

25 Claims, 14 Drawing Sheets

Related U.S. Application Data

(60) Provisional application No. 61/770,448, filed on Feb. 28, 2013.

(51) Int. Cl.
  *G09G 5/32* (2006.01)
  *G09G 5/36* (2006.01)
  *A61B 8/08* (2006.01)

(52) U.S. Cl.
  CPC ............. *A61B 8/467* (2013.01); *A61B 8/54* (2013.01); *G06F 1/1633* (2013.01); *G06F 1/1637* (2013.01); *G06F 1/1694* (2013.01); *G09G 5/32* (2013.01); *G09G 5/36* (2013.01); *A61B 8/0841* (2013.01); *G06F 2200/1614* (2013.01); *G09G 2340/0492* (2013.01); *G09G 2354/00* (2013.01); *G09G 2380/08* (2013.01)

(58) Field of Classification Search
  CPC .......... A61B 8/0841; G09G 5/36; G09G 5/32; G09G 2380/08; G09G 2340/0492; G09G 2354/00; G06F 2200/1614
  See application file for complete search history.

(56) References Cited

U.S. PATENT DOCUMENTS

| | | | |
|---|---|---|---|
| 5,623,931 | A | 4/1997 | Wung et al. |
| 5,758,650 | A | 6/1998 | Miller et al. |
| 5,924,988 | A | 7/1999 | Burris et al. |
| 5,924,992 | A | 7/1999 | Park et al. |
| 6,126,608 | A | 10/2000 | Kemme et al. |
| 6,139,496 | A | 10/2000 | Chen et al. |
| 7,141,020 | B2 | 11/2006 | Poland et al. |
| 7,244,234 | B2 | 7/2007 | Ridley et al. |
| 7,662,128 | B2 | 2/2010 | Salcudean et al. |
| 7,699,776 | B2 | 4/2010 | Walker et al. |
| 8,088,070 | B2 | 1/2012 | Pelissier et al. |
| 9,486,291 | B2 | 11/2016 | Bizzell et al. |
| 2004/0236217 | A1 | 11/2004 | Cerwin et al. |
| 2005/0085727 | A1 | 4/2005 | Swanborn |
| 2005/0249391 | A1 | 11/2005 | Kimmel et al. |
| 2006/0241430 | A1 | 10/2006 | Lin |
| 2007/0106156 | A1 | 5/2007 | Altmann et al. |
| 2007/0167808 | A1 | 7/2007 | Nozaki |
| 2007/0167829 | A1 | 7/2007 | Hirsh |
| 2007/0238998 | A1 | 10/2007 | Nycz et al. |
| 2007/0276253 | A1 | 11/2007 | Park et al. |
| 2008/0260227 | A1 | 10/2008 | Hayashi et al. |
| 2009/0024034 | A1 | 1/2009 | Moreau-Gobard et al. |
| 2009/0043204 | A1 | 2/2009 | Pelissier et al. |
| 2009/0187102 | A1* | 7/2009 | Di Marco ............ A61B 8/467 600/437 |
| 2009/0046912 | A1 | 12/2009 | Hostettler et al. |
| 2010/0016726 | A1 | 1/2010 | Meier |
| 2010/0040268 | A1 | 2/2010 | Boeing et al. |
| 2010/0179429 | A1 | 7/2010 | Ho et al. |
| 2010/0312120 | A1 | 12/2010 | Meier |
| 2011/0023585 | A1 | 2/2011 | Izikoff |
| 2011/0037866 | A1* | 2/2011 | Iwamoto ............ H04N 5/23219 348/222.1 |
| 2011/0054355 | A1 | 3/2011 | Hunter et al. |
| 2011/0125022 | A1 | 5/2011 | Lazebnik |
| 2011/0137175 | A1 | 6/2011 | Hossack et al. |
| 2011/0166451 | A1 | 7/2011 | Blaivas et al. |
| 2011/0313293 | A1 | 12/2011 | Lindekugel et al. |
| 2012/0029356 | A1 | 2/2012 | Hossack et al. |
| 2012/0289829 | A1 | 11/2012 | Barnes et al. |
| 2012/0293507 | A1 | 11/2012 | Inoue |
| 2012/0296213 | A1 | 11/2012 | Mauldin, Jr. et al. |
| 2013/0190624 | A1* | 7/2013 | Beger ............ A61B 8/462 600/443 |
| 2014/0005542 | A1 | 1/2014 | Bizzell et al. |
| 2015/0320391 | A1* | 11/2015 | Yao ............ A61B 8/467 600/424 |
| 2017/0000521 | A1 | 1/2017 | Bizzell et al. |

FOREIGN PATENT DOCUMENTS

| | | |
|---|---|---|
| CN | 102068275 | 5/2011 |
| DE | 102010047155 | 5/2011 |
| JP | 2007313114 | 12/2007 |
| JP | 2008284154 A | 11/2008 |
| JP | 2010119484 A | 6/2010 |
| WO | WO2001013796 | 3/2001 |
| WO | WO2002016963 A2 | 2/2002 |
| WO | 2006092594 A2 | 9/2006 |
| WO | WO2008071454 A2 | 6/2008 |
| WO | WO2009020617 | 2/2009 |
| WO | WO2010019795 A2 | 2/2010 |
| WO | WO2011094585 A1 | 8/2011 |
| WO | WO2012021542 A2 | 2/2012 |
| WO | WO2012148985 A1 | 11/2012 |
| WO | WO2012178109 A1 | 12/2012 |

OTHER PUBLICATIONS

F. W. Mauldin et al., "Three-dimensional spinal bone imaging with medical ultrasound for epidural anesthesia guidance", IEEE International Ultrasonics Symposium Proceedings, 2011, p. 238-241.

K. Owen et al., "Transducer Motion Estimation Using Combined Ultrasound Signal Decorrelation and Optical Sensor Data for Low-cost Ultrasound Systems with Increased Field of View", IEEE International Ultrasonics Symposium Proceedings, 2011, p. 1431-1434.

A. Rasoulian et al., "Augmentation of Paramedian 3D Ultrasound Images of the Spine", IPCAI, 2013, p. 51-60, Springer-Verlag Berlin Heidelberg.

I. Hacihaliloglu et al., "Automatic Bone Localization and Fracture Detection from Volumetric Ultrasound Images Using 3-D Local Phase Features", Ultrasound in Med. & Biol., 2012, p. 128-144, vol. 38, No. 1, World Federation for Ultrasound in Medicine & Biology.

A. Rasoulian et al., "Probabilistic Registration of an Unbiased Statistical Shape Model to Ultrasound Images of the Spine", SPIE, 2012, vol. 8316.

K. Owen et al., "Improved Elevational and Azimuthal Motion Tracker Using Sector Scans", IEEE Transactions of Ultrasonics, Ferroelectrics, and Frequency Control, Apr. 2013, vol. 60, No. 4, IEEE.

D. Shao et al., "Characteristic matching-based adaptive fast bilateral filter for ultrasound speckle reduction", Pattern Recognition Letters, 2013, p. 463-469, vol. 34, Elsevier.

S. Balocco et al., "SRBF: Speckle Reducing Bilateral Filtering", Ultrasound in Med. & Biol., 2010, p. 1353-1363, vol. 36, No. 8, Elsevier.

M. Lang et al., "Noise Reduction Using an Undecimated Discrete Wavelet Transform", IEEE Signal Processing Letters, Jan. 1996, p. 10-12, vol. 3, No. 1, IEEE.

S. Sudha et al., "Speckle Noise Reduction in Ultrasound Images Using Context-based Adaptive Wavelet Threshold", IETE Journal of Research, May/Jun. 2009, p. 135-143, vol. 55, Iss. 3.

F. W. Mauldin Jr., et al., "The Effects of Transducer Geometry on Artifacts Common to Diagnostic Bone Imaging with Conventional Medical Ultrasound", IEEE Transactions on Ultrasonics, Ferroelectrics, and Frequency Control, Jun. 2012, p. 1101-1114, vol. 59, No. 6, IEEE.

J. C. Lazaro et al., "Influence of thresholding procedures in ultrasonic grain noise reduction using wavelets", Ultrasonics, 2002, p. 263-267, No. 40, Elsevier Science B.V.

(56) References Cited

OTHER PUBLICATIONS

K. J. Chinn et al., "Ultrasound Imaging Facilitates Spinal Anesthesia in Adults with Difficult Surface Anatomic Landmarks", Anesthesiology, Jul. 2011, p. 94-101, vol. 115, No. 1.
US ISA, "International Search Report—Application No. PCT/US13/77917", WIPO, dated Mar. 20, 2014.
European Patent Office, "Partial Supplementary European Search Report—App. No. 13876155.6", dated Oct. 31, 2016, EPO.
European Patent Office, "Supplementary European Search Report—App. No. EP13876155", dated Apr. 20, 2017, EPO.

* cited by examiner

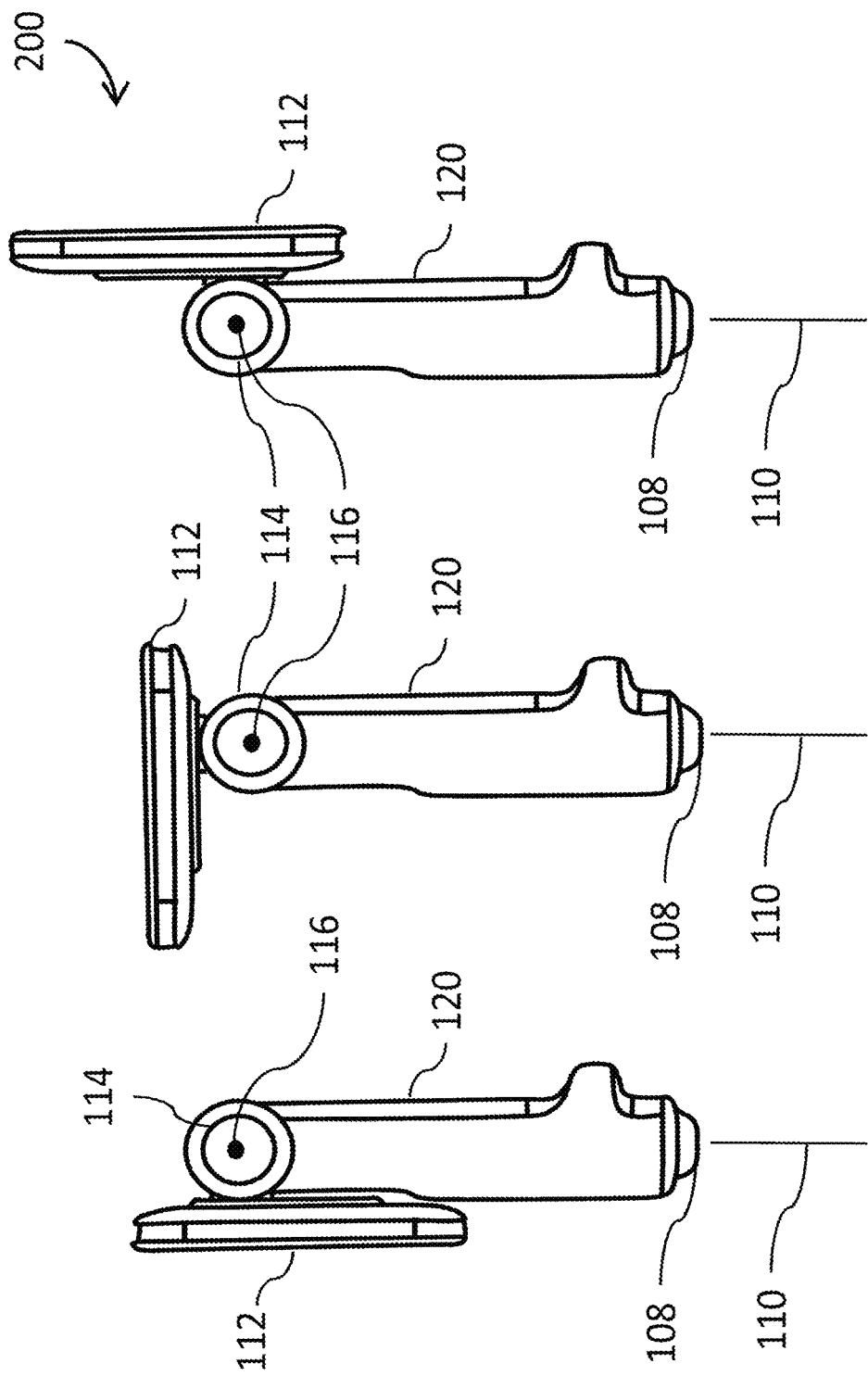

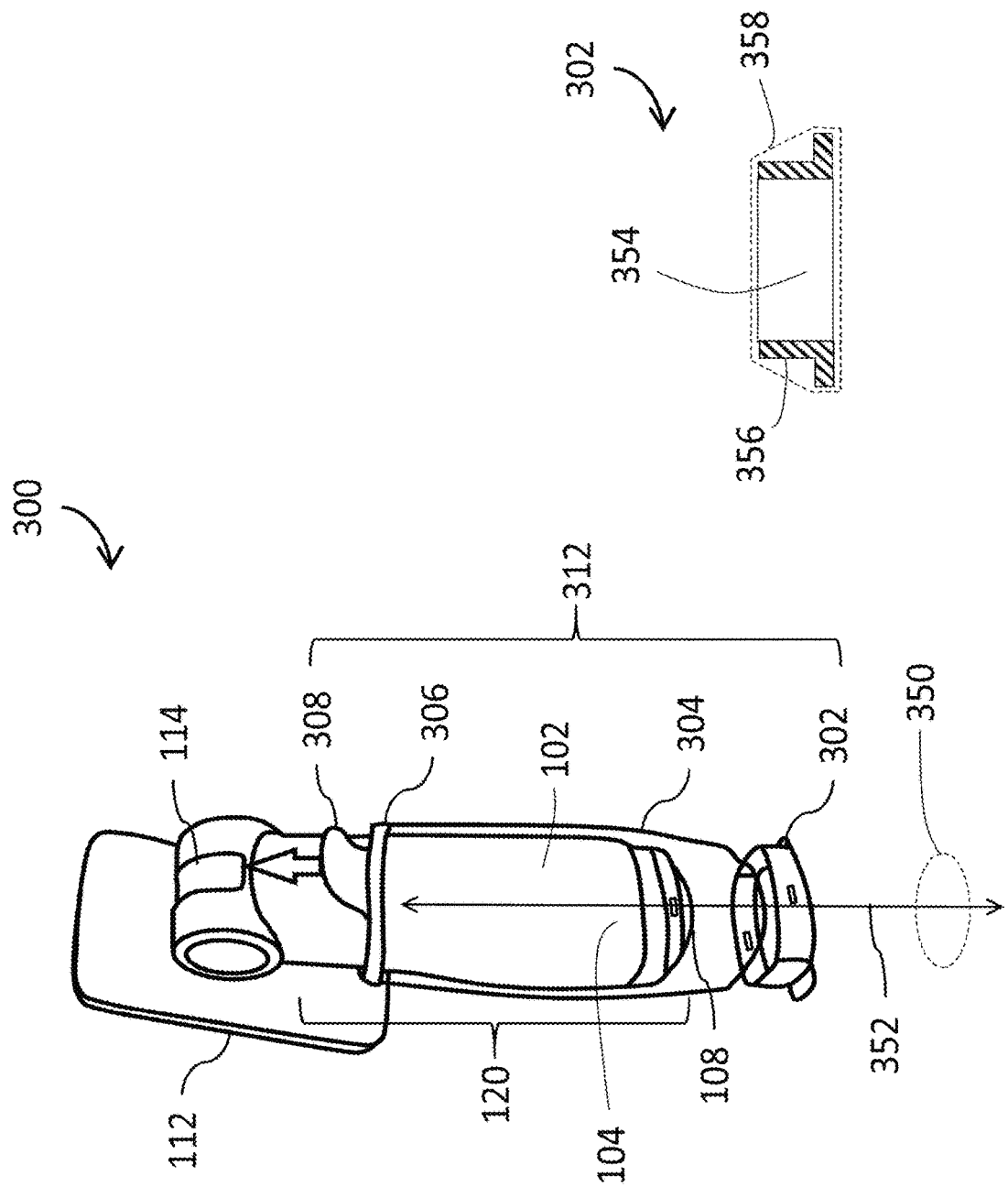

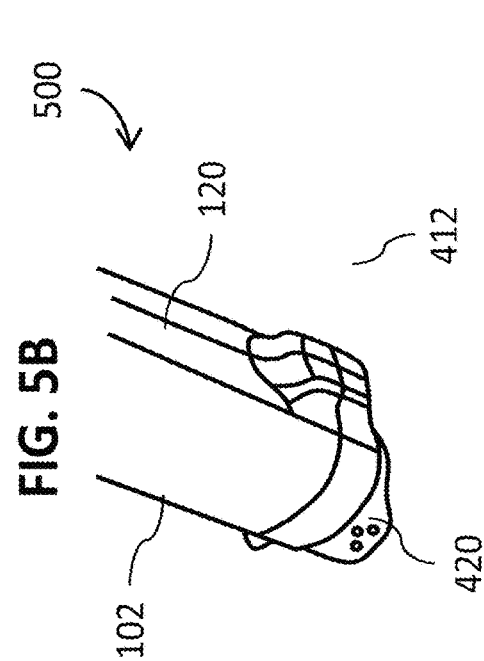
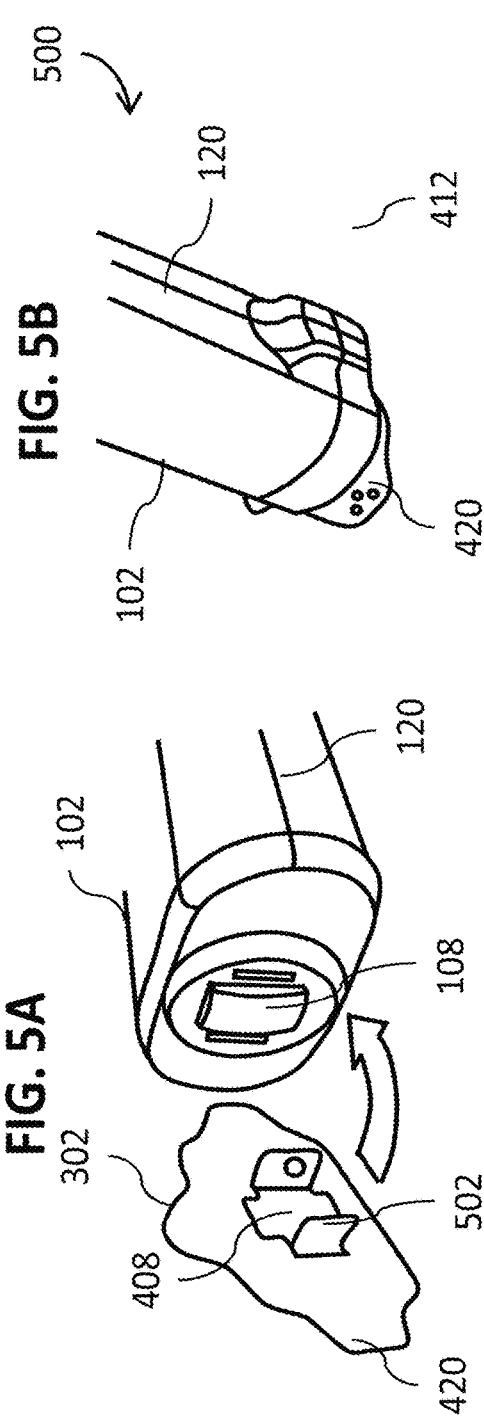
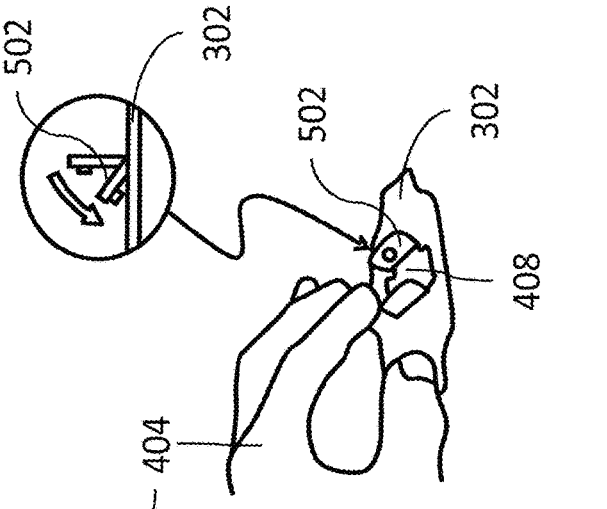
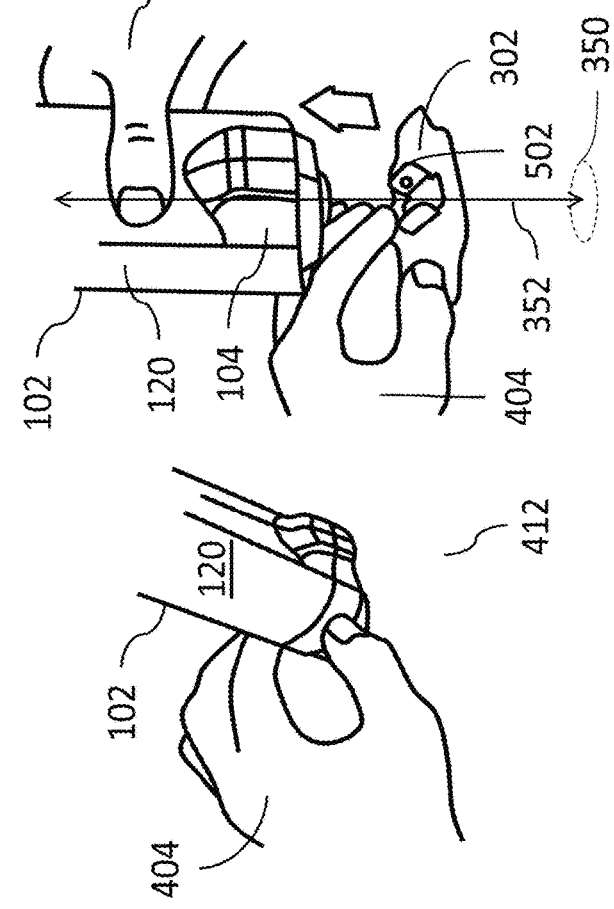

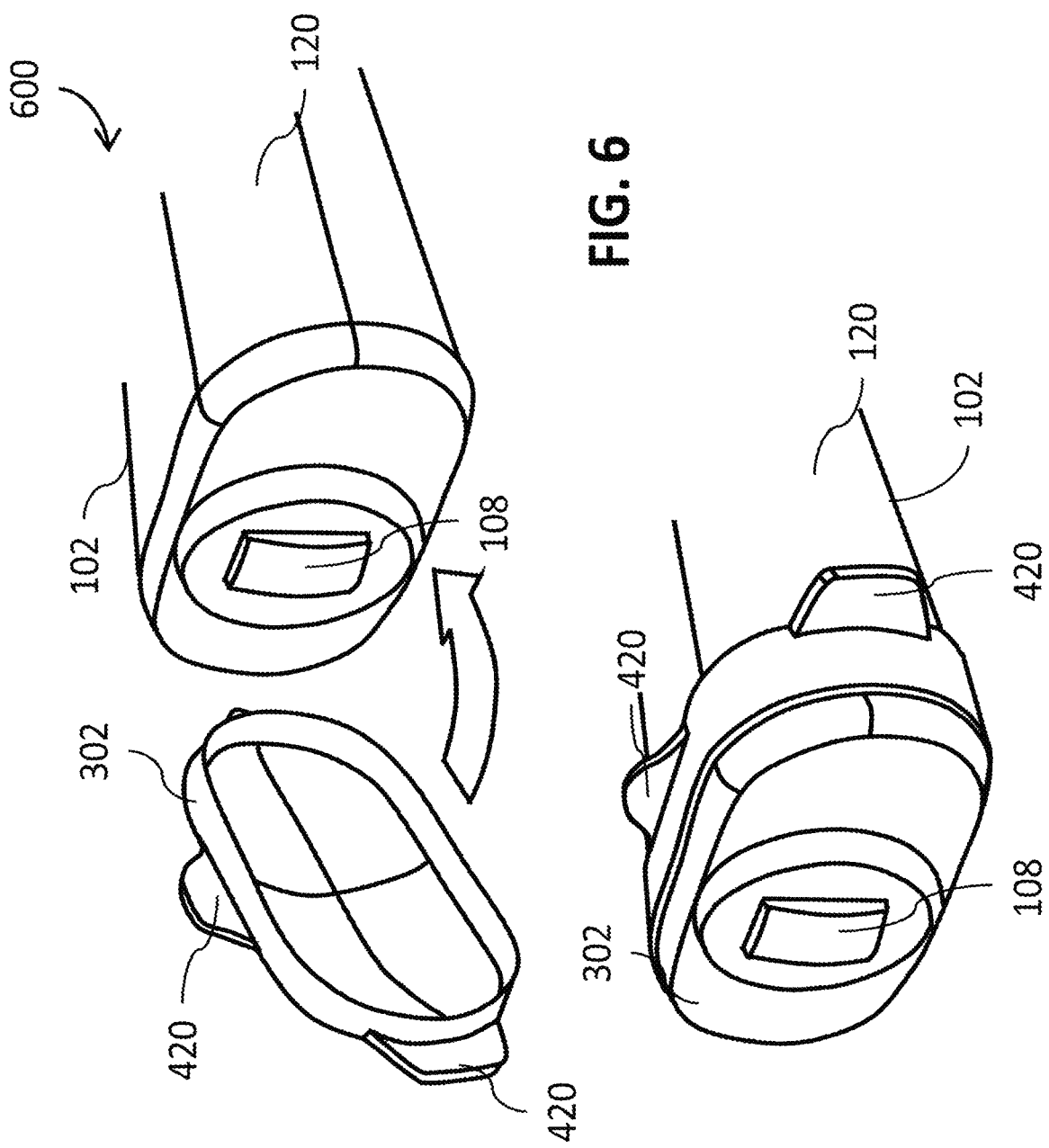

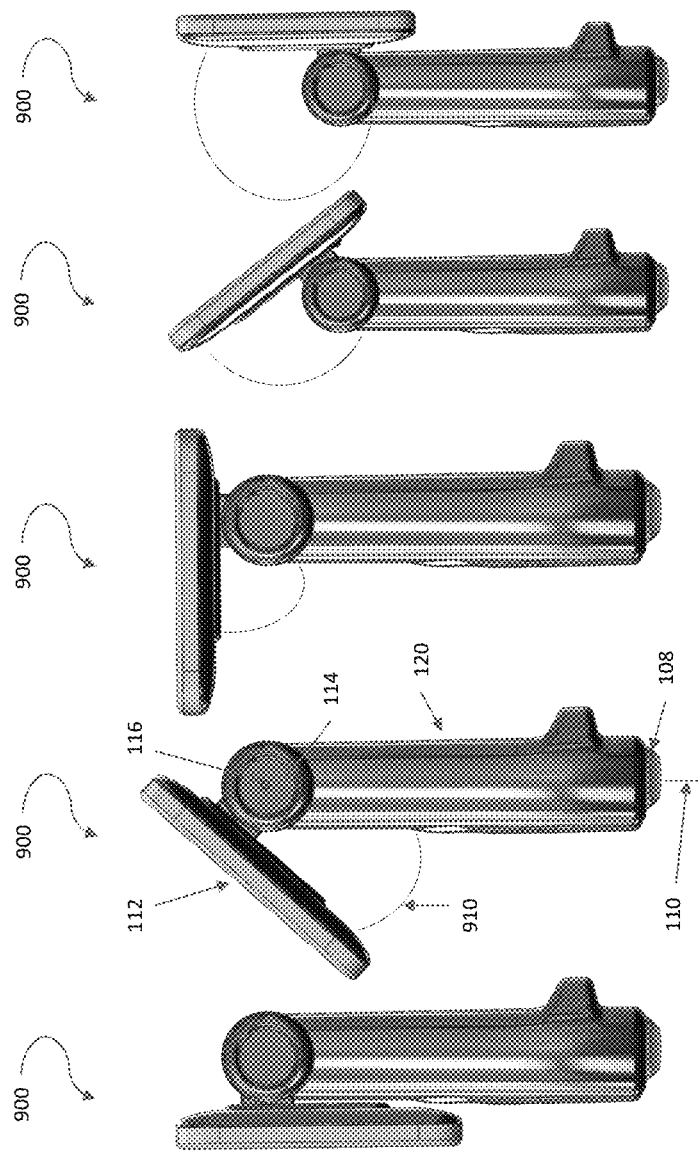

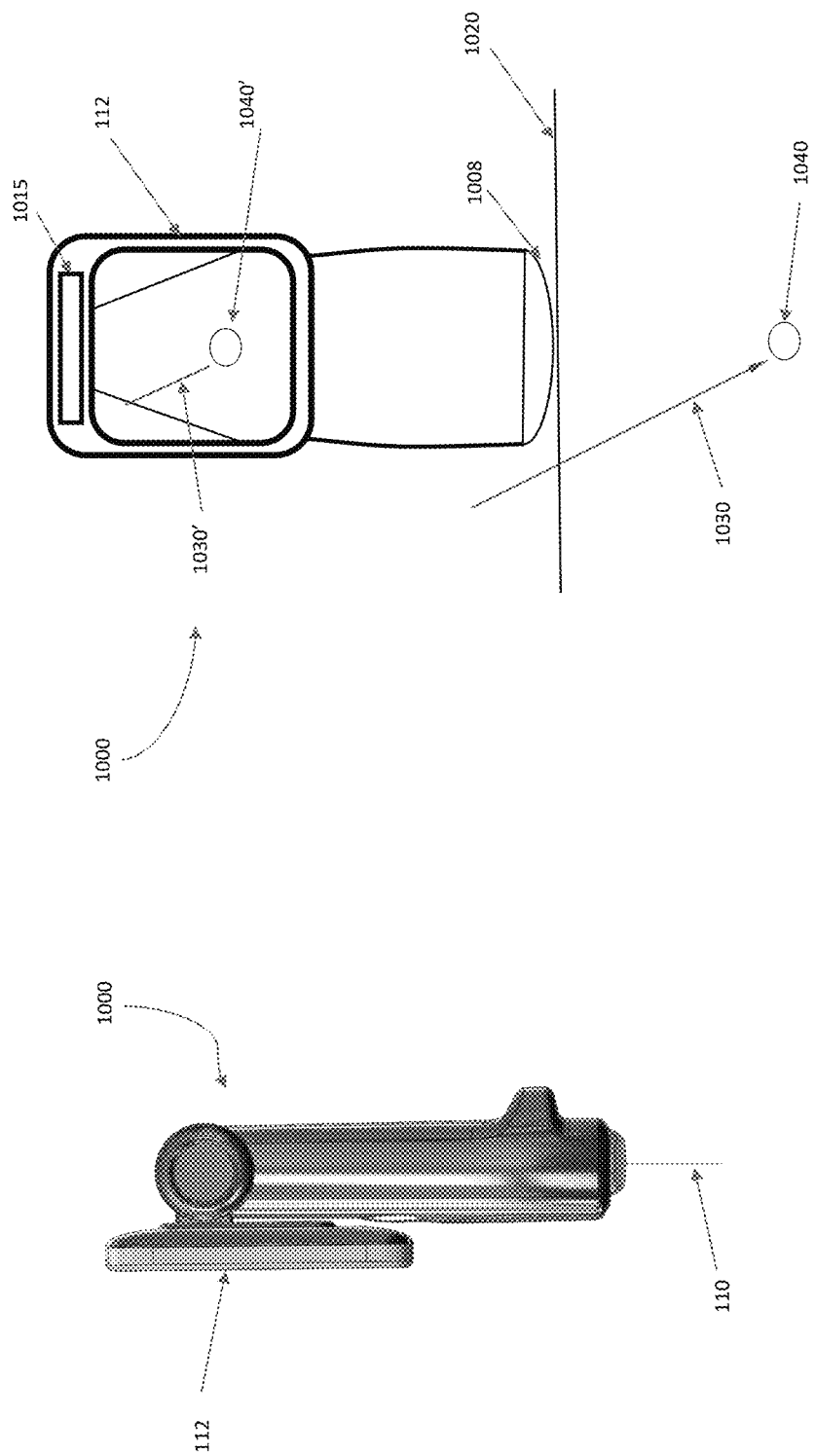

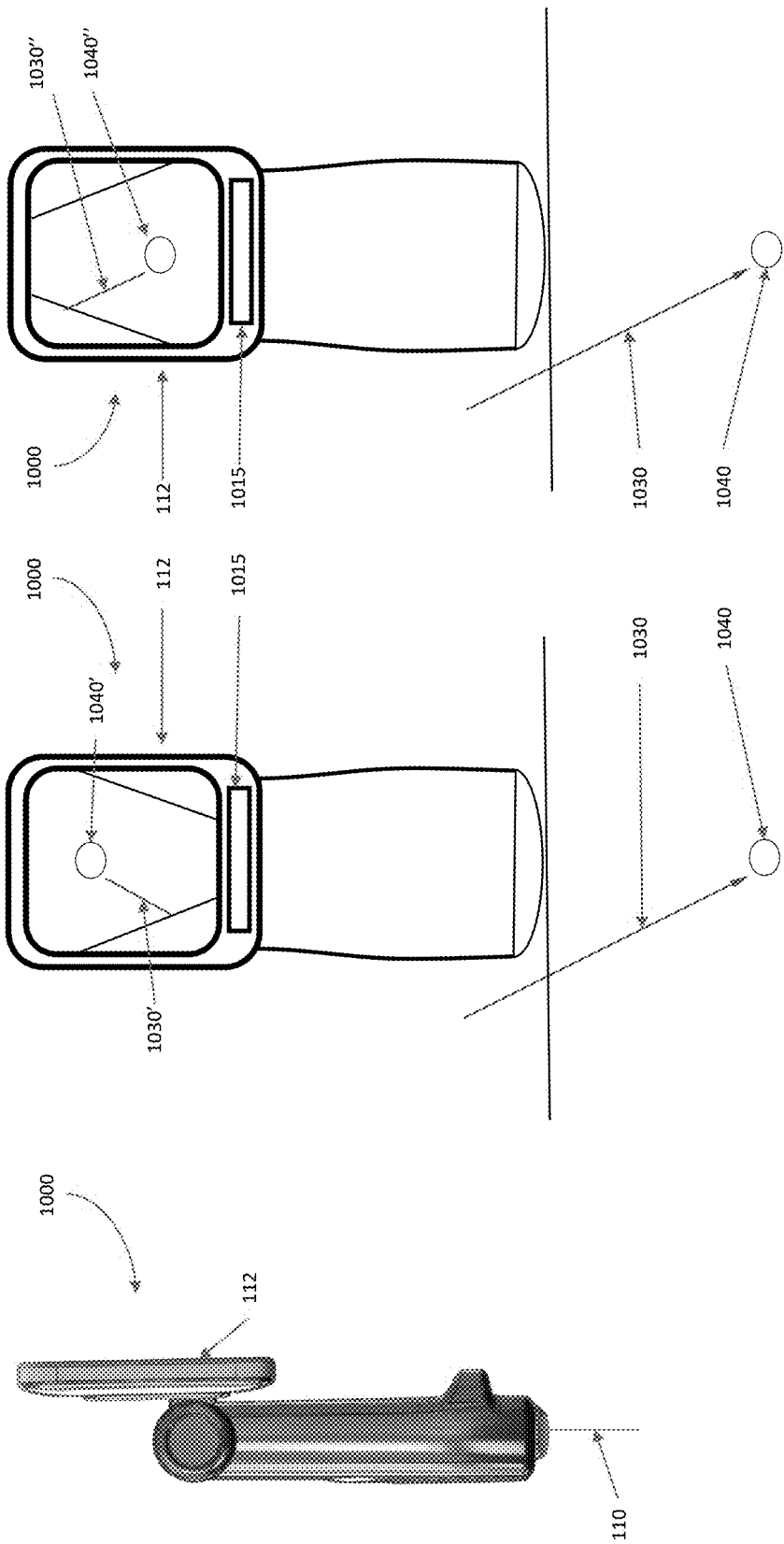

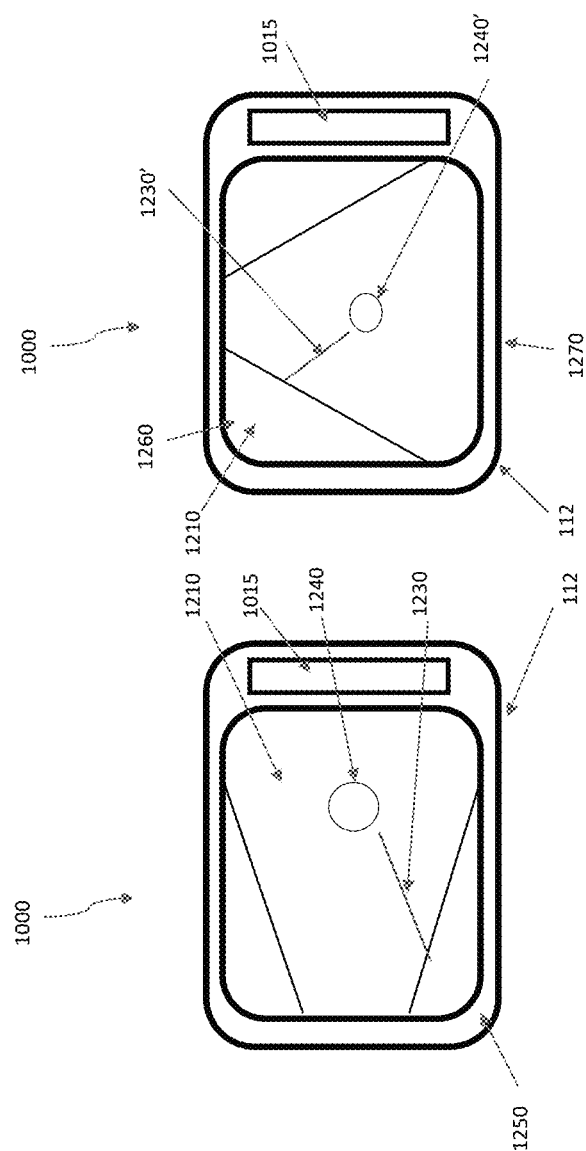
FIG. 12C
FIG. 12B
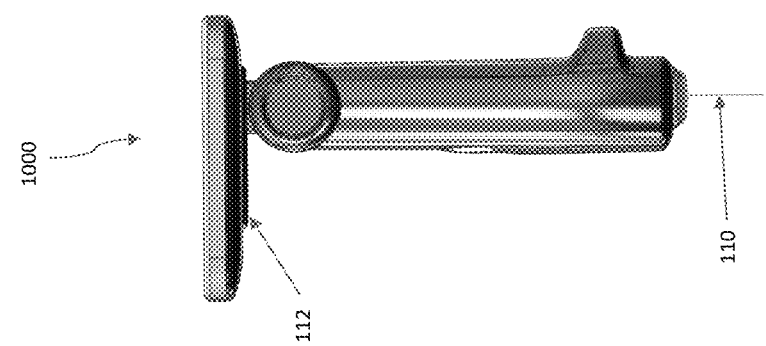
FIG. 12A

LOCALIZATION OF IMAGING TARGET REGIONS AND ASSOCIATED SYSTEMS, DEVICES AND METHODS

RELATED APPLICATIONS

The present application is a continuation-in-part of U.S. patent application Ser. No. 14/770,896, filed on Aug. 27, 2015, which, pursuant to 35 U.S.C. § 371, PCT Article 8 and PCT Rule 4.10, claims priority to, is related to, and is a U.S. national application based on International Application No. PCT/US2013/077917, filed on Dec. 27, 2013, now International Publication No. WO 2014/133665 A1, which, pursuant to 35 U.S.C. § 119(e), claims priority to U.S. Provisional Application No. 61/770,448, filed on Feb. 28, 2013. Each of the foregoing applications, each entitled "Localization of Imaging Target Regions and Associated Systems and Devices," is incorporated herein by reference in its entirety for all purposes.

GOVERNMENT SPONSORSHIP

This invention was made with government support under award number R43EB015232 awarded by the National Institute of Biomedical Imaging and Bioengineering of the National Institutes of Health and award number 1214788 awarded by the National Science Foundation. The government has certain rights in this invention.

TECHNICAL FIELD

Imaging devices and related methods for identification of target regions are generally described.

BACKGROUND

Medical ultrasound is a popular medical imaging modality primarily used for diagnostic imaging of soft tissue but also for interventional procedures such as guidance of a needle or catheter placement. Examples include diagnostic imaging of organs, such cardiac or liver structures. Common interventional procedures that rely on ultrasound guidance are central line placement and guidance of nerve blocks, both of which are high volume procedures in certain hospital settings such as the intensive care unit (ICU). Current ultrasound systems are mostly cart-based and optimized for superior contrast and resolution in soft tissue. However, these systems are generally expensive, and in a hospital setting with multiple physicians per ultrasound system, they can be difficult to access.

SUMMARY

Handheld ultrasound imaging devices are generally described. Certain embodiments have improved portability relative to prior imaging systems. In addition, attachable accessories that facilitate interventional procedures (including interventional ultrasound procedures) involving directing a probe (e.g., needle or catheter) to a probe target (e.g., blood vessel or nerve bundle) are also described. Certain embodiments can be used in handheld imaging devices, which address many of the limitations of prior art systems by, for example, providing standard imaging capabilities in a low cost portable device. The subject matter of the present invention involves, in some cases, interrelated products, alternative solutions to a particular problem, and/or a plurality of different uses of one or more systems and/or articles.

In one aspect, a handheld ultrasound-imaging device is provided. In certain embodiments, the handheld ultrasound imaging device comprises a housing comprising a first end comprising an ultrasound imaging unit, a second end comprising a display, and a hand grip region between the ultrasound imaging unit and the display.

The handheld ultrasound-imaging device comprises, according to some embodiments, a housing comprising an ultrasound imaging unit, a handgrip region, and a rotatable display, wherein the rotatable display is configured to be rotated, relative to at least another portion of the housing, about at least one rotational axis by at least about 30 degrees.

Any of the above handheld ultrasound imaging devices may comprise, according to some embodiments, an actuator on the handgrip region configured such that when the actuator is activated, data from the ultrasound-imaging unit is recorded and/or manipulated. The actuator may be, according to certain embodiments, configured to perform one or more of a number of other functions including, but not limited to, video save, device power on/off, image settings adjustment (e.g., imaging mode, gain, frequency, contrast, depth), and/or menu navigation.

Specifically, the apparatus described above and herein may be directed to a handheld ultrasound imaging device, comprising a housing comprising an ultrasound imaging unit; a hand grip region disposed on the housing between the display and the ultrasound imaging unit; and a rotatable display configured to be rotated, relative to at least another portion of the housing, about at least one rotational axis by at least 30 degrees, wherein the display is capable of displaying, in a plurality of image orientations, anatomical ultrasound images acquired by the ultrasound imaging unit.

The apparatus may further include a processor that is in electrical communication with the display, wherein the processor is configured to determine the image flip condition based at least in part on an input received from a user of the imaging device. Also, the processor may be configured to transmit an electronic signal to the display, said electronic signal instructing the display to display the anatomical ultrasound images in either the first image orientation or the second image orientation, depending on the image flip condition.

Yet another embodiment is directed to a method for displaying anatomical ultrasound images acquired by an ultrasound imaging unit, the method comprising in a handheld ultrasound imaging device comprising a housing comprising the ultrasound imaging unit, a processor and a rotatable display in electrical communication with the processor, said display configured to be rotated, relative to at least another part of the housing, about at least one rotational axis by at least 30 degrees in the processor, determining an image flip condition; the processor transmitting an electronic signal to the display, the electronic signal determined at least in part by the image flip condition; the display displaying the anatomical ultrasound images in a display orientation, the display orientation determined by the electronic signal received from the processor.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 2A-2C are, according to one set of embodiments, a series of schematic illustrations outlining the rotation of a display of an exemplary imaging device;

FIG. 3A is a schematic illustration of an imaging device comprising an exemplary detachable marking unit, according to some embodiments;

FIG. 3B is a schematic cross-sectional illustration of a marking unit, according to certain embodiments;

FIGS. 5A-5E are, according to certain embodiments, a series of schematic illustrations showing the use of an exemplary detachable marking unit;

FIG. 6 is a series of schematic illustrations showing the connectivity between an exemplary detachable marking device and an imaging device, according to one set of embodiments;

FIGS. 9A-9E are side views of an exemplary imaging device with a rotatable display screen shown in various rotational positions;

FIGS. 10A-10B are side and front views, respectively, of an exemplary imaging device, with FIG. 10B showing on the display screen ultrasound images acquired from a subject;

FIG. 11A is a side view, and FIGS. 11B-11C are rear views, of the imaging device of FIGS. 10A-10B, with the display screen rotated 180 degrees from its position as shown in FIGS. 10A-10B, with FIGS. 11B-11C showing on the display screen ultrasound images acquired from a subject, wherein the images are flipped in FIG. 11C from the orientation in which they appear in FIG. 11B;

FIG. 12A is a side view, and FIGS. 12B-12C are top views, of an exemplary ultrasound imaging device, with FIGS. 12B and 12C showing on the display screen thereof ultrasound images acquired from a subject, wherein the images are rotated 90 degrees in FIG. 12C from the orientation in which they appear in FIG. 12B;

DETAILED DESCRIPTION

Figure 1:
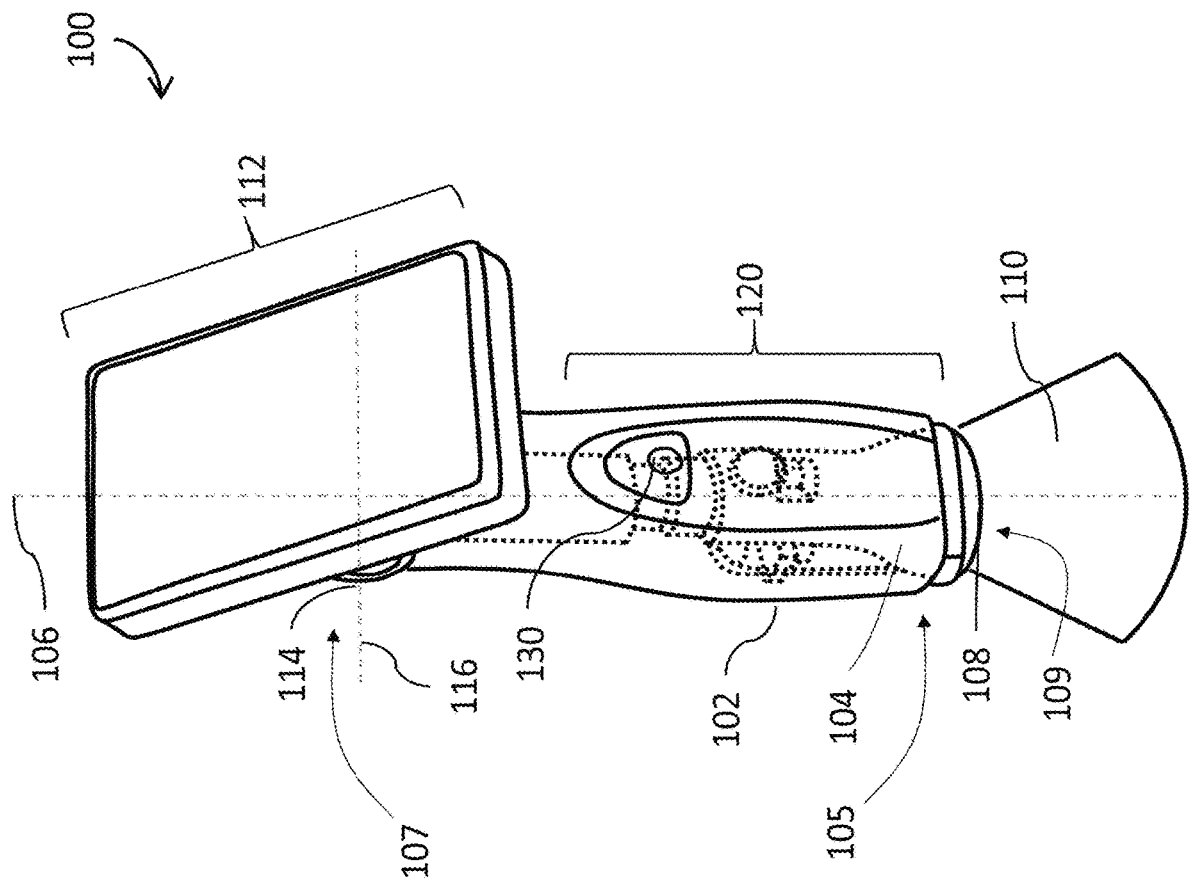
FIG. 1 is a schematic illustration of an exemplary imaging device, according to certain embodiments.

Imaging devices and related methods for identification of target regions are generally described. Certain embodiments relate to handheld ultrasound imaging devices. Various embodiments are related to configurations that may provide, in some cases but not necessarily all cases, one or more advantages during operation of the imaging device.

Certain embodiments are related to handheld ultrasound imaging devices in which the imaging unit, the display, and the handgrip region are positioned relative to each other such that operation of the imaging device is made easier, under certain circumstances. In one set of embodiments, the handheld ultrasound imaging device comprises a housing, which can include an ultrasound imaging unit at one end, a display at another end, and a handgrip region between the ultrasound imaging unit and the display. As described in more detail below, arranging the imaging unit, the hand grip region, and the display in this manner can allow one to direct the movement of the handheld device relatively easily (e.g., by resting the side of the hand on a surface of the object that is being imaged) while maintaining the ability to see the display screen.

Certain embodiments are related to the use of rotatable displays in handheld ultrasound imaging devices. Generally, ultrasound-imaging devices in the past have included fixed displays or displays that are spatially separated from the housing in which the imaging unit is contained. Imaging devices with fixed displays can be difficult to operate, as they do not allow one to adjust the angle of the display relative to the eye of the user without rotating or otherwise moving the housing to which the display is connected. While imaging devices with displays that are spatially separated from the device housing allow one to adjust the position of the display relative to the imaging unit, they are generally difficult to transport and/or store when they are not in use. By integrating the display with the housing while maintaining the ability to rotate the display relative to the housing one can realize the benefit of portability and ease of storage while also allowing for relatively easy repositioning of the display relative to the user's eye.

Some embodiments are directed to inventive configurations of marking units—configured to direct the placement of a probe such as a needle or catheter—in the handheld ultrasound imaging devices. For example, according to certain embodiments, a handheld ultrasound imaging device can comprise a marking unit detachably coupled to the housing of the device and positioned such that the target that is being imaged, the ultrasound-imaging unit, and the marking unit are aligned during use. Maintaining alignment of these components can allow one, according to certain embodiments, to properly align the marking unit relative to the target relatively easily during use. As described in more detail below, this alignment, according to some embodiments, may allow one to position the marking unit while the imaging unit is still in place, which can, according to certain embodiments, improve the accuracy of the placement of a probe such as a needle, a catheter, or other device.

FIG. 1 is an exemplary schematic illustration of a handheld ultrasound-imaging device 100, according to certain embodiments. In certain embodiments, the handheld ultrasound imaging device comprises a housing. For example, in FIG. 1, imaging device 100 comprises housing 102. According to certain embodiments, the housing comprises a first end associated with an ultrasound-imaging unit. Referring to FIG. 1, for example, imaging unit 104 is associated with end 105 of housing 102. As shown in FIG. 1, ultrasound-imaging unit 104 is enclosed within housing 102. Other arrangements are also possible.

In some embodiments, imaging unit 104 can comprise, for example, an ultrasound transducer 108. The ultrasound-imaging unit 104 can be configured, in certain embodiments, to produce an image along at least one scanning plane 110. The imaging unit can be configured to produce an image using standard ultrasound image processing techniques known to those of ordinary skill in the art of ultrasound imaging, and described in more detail below.

The imaging device 100 comprises, in certain embodiments, display 112 (e.g., an LCD display, an OLED display, or any other suitable type of display). The display can be located at a second end of the housing. For example, in FIG. 1, display 112 is located at end 107 of housing 102. According to certain embodiments, ultrasound transducer 108 can be configured to produce data along at least one scanning plane 110 that can be subsequently output on display 112.

In certain embodiments, an ultrasound transducer surface (e.g., configured to be applied on or near a target site) can be located at one end of the housing and the display can be attached to the housing at the opposite end. For example, in FIG. 1, ultrasound transducer surface 109 is located at end 105 of housing 102, and display 112 is located at second end 107 of housing 102. In certain embodiments, the display can be directly attached to the top of the housing. For example, in FIG. 1, display 112 is directly attached to the top of housing 102.

According to certain embodiments, the display of the imaging unit can be a rotatable display. For example, referring to FIG. 1, display 112 can be connected to housing 120 via pivot 114, which can allow rotatable display 112 to rotate about at least one rotational axis 116. Any suitable pivot may be used. For example, as shown in FIG. 1, cylindrical pivot 114 can be used to rotate display 112 about a single rotational axis 116. FIGS. 2A-2C are exemplary schematic illustrations showing the rotation of display 112 about single rotational axis 116 (going into and out of the page in FIGS. 2A-2C). In FIGS. 2A-2C, display 112 of imaging device 200 is rotated about device handgrip region 120. In certain embodiments, pivot 114 comprises a ball-and-socket arrangement or other type of arrangement, which can allow for rotation of display 112 about multiple rotational axes. In some such embodiments, display 112 can be rotated about more than one axis so that twisting or rotation in other dimensions is allowed. In other such embodiments, the display 112 can be attached to the housing via magnets, hook and loop fastener (e.g., Velcro), or other attachment means.

In some embodiments, the rotatable display is configured to be rotated, relative to at least another portion of the housing (e.g., the handgrip region, the imaging unit, and/or another portion of the housing), about at least one rotational axis by at least about 30 degrees, at least about 60 degrees, at least about 90 degrees, at least about 120 degrees, at least about 150 degrees, or at least about 175 degrees. For example, in FIGS. 2A-2C, display 112 is illustrated as being rotated about both handgrip region 120 and ultrasound transducer 108 by 180 degrees.

In certain embodiments, the rotatable display is configured to be rotated such that the display can be oriented in a first position substantially parallel to a scanning plane of the imaging unit and in a second position substantially perpendicular to the scanning plane of the imaging unit. For example, in FIGS. 2A and 2C, imaging device 100 is shown in which display 112 is substantially parallel to scanning plane 110 of imaging device 100. In addition, in FIG. 2B, display 112 is substantially perpendicular to scanning plane 110 of imaging device 100. Display 112 can be said to be in a 0-degree configuration in FIG. 2A, a 90-degree configuration in FIG. 2B, and a 180-degree configuration in FIG. 2C. In the exemplary embodiment of FIGS. 2A-2C, display 112 can be configured to a position at any angle relative to scan plane 110 of imaging device 100 within the range between the 0-degree configuration (FIG. 2A) and the 180-degree configuration (FIG. 2C).

While a rotatable display has been described in association with the above embodiments, it should be understood that the invention is not so limited, and in other embodiments, non-rotatable displays could be used.

In certain embodiments, the housing is elongated and comprises a longitudinal axis. For example, referring back to FIG. 1, housing 102 is elongated and comprises longitudinal axis 106.

In some embodiments, the imaging device is configured such that the smallest angle between the scanning plane 110 of the ultrasound imaging unit 104 and the longitudinal axis 106 of the device housing 102 is relatively small (e.g., less than about 45°, less than about 30°, less than about 15°, less than about 5°). In certain embodiments, the smallest angle between the scanning plane 110 of the ultrasound imaging unit 104 and the longitudinal axis 106 of the device housing 102 is less than about 1°, in which case, the scanning plane 110 of the ultrasound imaging unit 104 is said to be substantially parallel to the longitudinal axis 106 of the device housing 102.

In some embodiments, the imaging device can be relatively small. For example, in certain embodiments, the imaging device may occupy a volume of equal to or less than about 500 cm$^3$ or less than about 100 cm$^3$ (as determined by sealing any openings on the external surfaces of the imaging device and measuring the volume of liquid displaced by the sealed imaging device). In some embodiments, the imaging device is configured such that the entire device may be arranged to fit into a pocket. For example, the ultrasound imaging device can be configured such that the entire device fits into a side pants pocket, according to certain embodiments.

In some such embodiments, the imaging device is portable such that it may be, for example, carried or otherwise manipulated by hand (e.g., by a single hand). In some embodiments, the imaging device is completely self-contained with portable dimensions such that it can be manipulated with one hand.

In certain embodiments, the housing comprises a hand grip region (e.g., a handle), which can be configured to be grasped by the user during operation of the imaging device. In some embodiments, the hand grip region can be between the ultrasound imaging unit and the display. For example, referring to FIG. 1, hand grip region 120 of imaging device 100 is positioned between imaging unit 104 and display 112. In certain embodiments, the hand grip region may be between the imaging interface of the ultrasound transducer and the display. The imaging interface of an ultrasound transducer is known to those of ordinary skill in the art to refer to the interface of the transducer from which the ultrasonic signal emanates. For example, referring to FIG. 1, ultrasound transducer 108 comprises imaging interface 109.

The hand grip region (e.g., handle) may be positioned, in certain embodiments, such that it is directly above the imaging unit during operation of the imaging device. For example, referring to FIG. 1, hand grip region 120 is positioned such that it is directly above imaging unit 104 (as well as transducer 108 and imaging interface 109 of transducer 108) during operation of imaging device 100.

In some embodiments, the imaging device can be battery operated. For example, in certain embodiments, the imaging device is powered using a cell-phone class battery, such as a 2000 mAh Li-ion battery.

In certain embodiments the display can be integrated with the device housing (e.g., such that display and the device housing form a monolithic unit). For example, referring to FIG. 1, device housing 102 is integrated with imaging unit 104 (and transducer 108) to form an integrated, monolithic unit. In addition, in FIG. 1, display 112 and device housing 102 are integrated to form a monolithic unit. In other embodiments the display can be detachable from the housing unit. In some such embodiments, the ultrasound imaging unit (e.g., 104 in FIG. 1) can communicate with the display via wireless connection.

Certain of the imaging devices described herein can provide one or more of a variety of advantages, relative to prior devices. For example, according to certain embodiments, by attaching the display to the base of the housing (e.g., in direct contact with the base of the housing), the display can be located relatively close to the target site that is being imaged (e.g., a subject such as a human subject). This can make, according to certain embodiments, operation of the inventive imaging device easier than systems that include, for example, a transducer probe with a cable and the display that is not in the same vicinity as the user's hand and probe. In certain embodiments, the closest distance between the image display and the target site (e.g., skin surface 412 in FIGS. 4A-4D) is less than about 1 meter, less than about 500 cm, less than about 100 cm, less than about 50 cm, or less than about 25 cm.

Certain of the embodiments described herein do not include a separate transducer-to-display cable, which would otherwise complicate operation and handling of the imaging device. In addition, as noted above, the imaging device can be configured to be portable and adopt a form factor that can be more easily transported in a user's pocket. While other handheld ultrasound devices have been proposed with an attached screen (i.e., no transducer-to-display cable), such systems possess a form factor where the hand is placed along a handle region that is extended from the transducer face. That is to say, in such systems, the longitudinal axis of the handle forms a smallest angle with the imaging plane of the imaging unit that is close to 90 degrees. In contrast, certain of the embodiments described herein place the hand immediately above the transducer face, which possesses the benefit of allowing for finer control of the scan plane. That is to say, certain of the embodiments described herein include a smallest angle between the longitudinal axis of the hand grip region and the imaging plane of the imaging unit that is relatively small (e.g., a smallest angle of less than about 45°, less than about 30°, less than about 15°, or less than about 5°) and/or are configured such that the longitudinal axis of the hand grip region is substantially parallel to the imaging plane of the imaging unit. Those of ordinary skill in the art are familiar with the longitudinal axis of a hand grip region, which refers to the elongated axis around which the hand grasps when grasping the handgrip region. In certain embodiments, the longitudinal axis of the handgrip region corresponds to the longitudinal axis of the housing in which the handgrip region is formed.

According to certain embodiments, there may be a clinical benefit to using an ultrasound imaging device in which the display screen is housed within the same device housing as the imaging unit and/or is rotatable about the longitudinal axis of the device. In some embodiments, the rotating display can allow the user to adjust the display angle to account for different angles between the user's eye level and the central longitudinal axis of the device. Thus, the user may hold the imaging device above, below, to the left of, or to the right of their eye level and still have a good viewing angle to the display. The ability to adjust the eye level can be important for scanning different anatomies with the same device while still being able to view the display screen. As one example, performing a cardiac scan and a lumbar spine scan while maintaining the user's body in a substantially fixed position (e.g., standing or sitting) will generally necessitate positioning the imaging device such that the angle between the device and the user's eye level varies. Without a rotatable screen, the user would need to substantially move their body orientation in order to view the screen with sufficient clarity for both types of scans. With the rotatable screen, however, there is greater flexibility in uses of the ultrasound device, while maintaining a smaller form factor compared with ultrasound devices that have a separate transducer and display screen connected by a cable.

Moreover, positioning the hand grip region as illustrated in FIG. 1 (and other figures) can produce greater control over the position of the scan plane and/or can facilitate clinical acceptance. Precise control over the scan plane relative to the anatomy of interest is often important in ensuring that the anatomy is accurately captured by the scan plane and can be assessed via review of the display screen. In certain embodiments in which the hand grip region is configured such that the longitudinal axis of the hand grip region is substantially parallel to the imaging plane, the user's hand can be used to control the imaging device by placing the hand on the hand grip region while also resting the hand on the target skin surface. During testing of this configuration, it was discovered that arranging the imaging unit components in this manner leads to greater stability. Without wishing to be bound by any particular theory, it is believed that this increase in stability is observed because the hand, target skin surface, and device are all connected and can all move together. Frequently, a subject (e.g., a patient) may move during an ultrasound scan (e.g., due to discomfort, restlessness, or for another reason). Certain embodiments, including that illustrated in FIG. 1 and other figures can allow for a stable image to be captured regardless of patient motion.

In certain embodiments, the imaging device comprises an actuator on the hand grip region configured such that when the actuator is activated, data from the ultrasound imaging unit is recorded and/or manipulated. For example, in FIG. 1, imaging device 100 comprises actuator 130, which is in the form of a button. According to certain embodiments, when actuator 130 is depressed, data from the ultrasound imaging unit is recorded, for example, to memory within the ultrasound imaging device or to an external memory unit outside the imaging device (e.g., after being transported via a wireless or wired connection between the imaging unit and the external memory unit). The data from the ultrasound imaging unit that is recorded can correspond to, for example, imaging data (e.g., data related to a B-mode image, a C-mode image, an M-mode image, a tissue harmonic image, a three-dimensional image, a Color Doppler image, a Power Doppler image, a Pulse-wave Doppler image, a continuous wave Doppler image, an ultrasound contrast agent enhanced image, a B-flow image, or any other type of image). In this way, the actuator can be configured to take a "snapshot" of the data being collected by the ultrasound imaging device at that point in time during its use. In some embodiments, the actuator can be configured to perform one or more of a number of other functions including: video save, device power on/off, image settings adjustment (e.g., imaging mode, gain, frequency, contrast, depth), and/or menu navigation. In some embodiments, the imaging device 100 comprises a plurality of actuators, such as the actuator 130 in FIG. 1, which can perform different functions, such as the aforementioned functions.

While the actuator illustrated in FIG. 1 is a button, any suitable actuator type can be used. Examples include, but are not limited to, touch sensors (e.g., resistive, capacitive, optical), switches, proximity sensors, and/or optical sensors.

It can be advantageous, according to certain but not necessarily all embodiments, to locate the actuator on the hand grip region of the imaging device. Locating the actuator on the hand grip region can allow a user to activate the data saving function, or other aforementioned functions, relatively easily, for example, by simply activating the actuator using a digit of the hand (e.g., a finger and/or thumb) holding the imaging device. In some embodiments, the hand may activate the actuator for purposes of activating a desired function, such as a saving function, simultaneously while performing an image scan without requiring the user to reorient the hand on the hand grip region of the ultrasound device. That is to say, according to certain embodiments, the user does not need to reorient their hand to save an image during an ultrasound scan.

According to certain embodiments, the imaging device comprises a marking unit detachably coupled to the housing. For example, in FIG. 3A, imaging unit 300 comprises marking unit 302, which can be detachably coupled to housing 102. Similar arrangements are illustrated in the embodiments shown in FIGS. 4A-4D, 5A-5E, 6, and 7, described in more detail below.

The marking unit and the housing can be detachably coupled in any suitable fashion. In some embodiments, the marking unit can be indirectly coupled to the housing. For example, as described in more detail below, according to certain embodiments, a cover body is attached to the housing. In some such embodiments, the marking unit is detachably coupled to the cover body. Exemplary embodiments of such an arrangement are illustrated in FIGS. 3A and 4A-4D. In certain embodiments, the marking unit is present alone, without the cover body. In some such embodiments, the marking unit is directly coupled to the housing. For example, in FIGS. 5A-5E and 6, marking unit 302 is directly coupled to the housing of the imaging unit. The marking unit can be "self-attaching" to the imaging device (or the cover body, when present), in certain embodiments. That is to say, in some embodiments, substantially no separate attaching material (such as a rubber band) is required to attach the marking unit to the imaging device (or to the cover body, when present). Examples of mechanisms that can be used to attach the marking unit to the imaging device (and/or the cover body, when employed) in this way include, but are not limited to, magnetic fittings (e.g., a pair of magnets between the housing and the marking unit), mechanical attaching mechanisms (such as a fitted plastic inserts, spring-loaded retaining clips, frictional fittings, elastic bands, hook and loop fasteners, screw threads), and the like. Of course, other attachment mechanisms, such as adhesive-based attachment mechanisms, could also be used.

The marking unit can be configured to indicate proper placement of a probe (e.g., a needle and/or a catheter) along a target that is to be imaged, in some embodiments. In certain embodiments, the marking unit is configured to identify a target surface location (e.g., an insertion location) corresponding to a center of an imaging scan plane. The marking unit can comprise, in certain embodiments, a probe indicator configured to indicate proper placement of a probe at or near a target that is to be imaged. For example, in some embodiments, the marking unit comprises an identifying mark indicating the target surface location. The identifying mark can comprise, for example, a hole, an indentation, or other identifying mark.

In some such embodiments, the detachable marking unit can be mechanically removed from the imaging device during use. In some such embodiments, the detachable marking unit 302 can be left at or near the target site (e.g., on the skin) to identify the center of the transducer along the skin after the transducer itself has been removed.

Figures 4A, 4B, 4C, 4D:
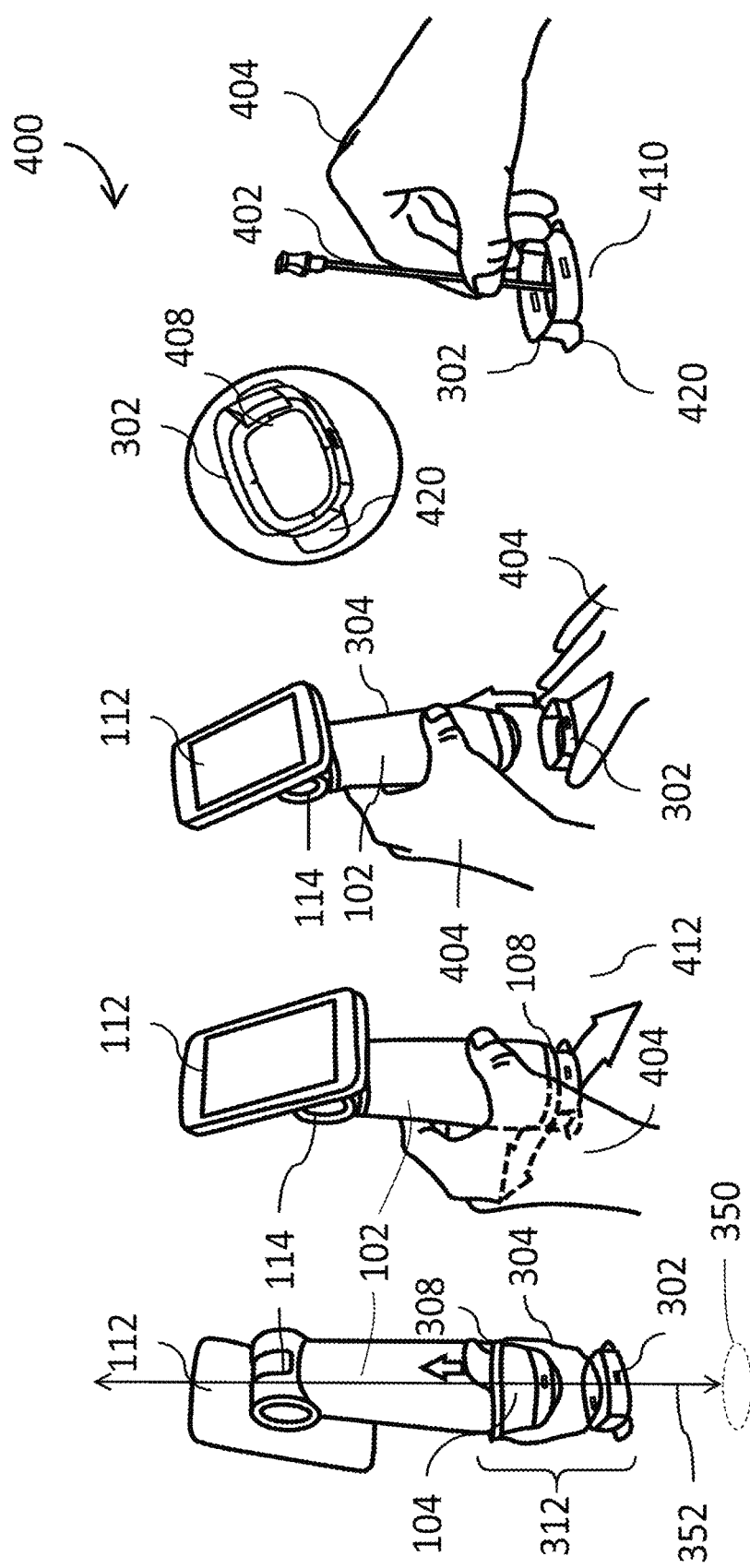
FIGS. 4A-4D are a series of schematic illustrations showing the use of an exemplary detachable marking unit, according to certain embodiments.

FIGS. 4A-4D are exemplary schematic illustrations outlining such use of the detachable marking unit. In FIG. 4A, the detachable marking unit is used to identify the location of needle insertion (i.e. the target insertion location 410) in a spinal anesthesia procedure, although use of the detachable marking unit to locate other types of target anatomy (e.g., blood vessels, nerves, joints, or organ tissues) is also possible. In FIG. 4A, marking unit 302 is placed over an imaging device hand grip region 120. Marking unit 302 can be configured to indicate proper placement of a needle (shown as 402 in FIG. 4D) along a target skin surface 412, which is to be the imaging surface, in some embodiments.

As shown in FIG. 4B, ultrasound imaging device 100 can be scanned across target skin surface 412 with a user's hand 404 until the user identifies the target anatomy in the ultrasound image displayed on device display 112. According to certain embodiments, marking unit 302 can be configured to identify a location along skin surface 412 that corresponds to the center of the scanning plane produced by ultrasound transducer 108 of the imaging device.

Next, as illustrated in FIG. 4C, marking unit 302 can be detached by user's hand 404 from both the device hand grip region 120 (and optional cover body 304, described in more detail below). In certain embodiments, the marking unit is configured to be attached to a target surface. For example, in some embodiments, the marking unit comprises an adhesive material configured to adhere the marking unit to a surface of a target (e.g., the skin of a subject). In FIG. 4C, for example, marking unit 302 can comprise an adhesive material configured to adhere marking unit 302 to skin surface 412. Other attachment mechanisms could also be employed. For example, in some embodiments, the marking unit comprises a vacuum-generating unit configured to adhere the marking unit to a surface associated with the target. The marking unit 302 can comprise, for example, suction cups or other vacuum means to support adhesion of the marking unit to the target surface.

As noted above, in certain embodiments, the marking unit comprises, a probe indicator configured to indicate proper placement of a probe at or near a target that is to be imaged. For example, in some embodiments, the marking unit comprises an identifying mark indicating the target surface location. The identifying mark can comprise, for example, a hole, an indentation, or other identifying mark. In FIG. 4D, marking unit 302 comprises identifying marks 408, which are configured to indicate the proper placement of needle 402 along skin surface 412. In certain embodiments, the marking unit 302 comprises a hole 408 in the middle where the center of the transducer 108 was located when the unit 302 was detached from the imaging device housing, such that when left on skin 412, marking unit 302 identifies the place along skin surface 412 corresponding to the center of ultrasound scan plane 110.

According to certain embodiments, with the marking unit 302 adhered to the skin surface 412, the user can insert a probe 402 at the target insertion location 410 using the hole guide 408 along the marking unit 302.

The detachable marking unit, in some embodiments, can comprise a wing component. For example, referring to FIG. 4D, detachable marking unit 302 comprises wing 420. The wing component can be advantageous, according to certain although not necessarily all embodiments, because it can improve one's ability to adhere the marking unit to a target skin surface by increasing surface area of the marking unit along the target skin surface.

While identifying marks are illustrated in FIG. 4D as guiding the placement of the probe, other embodiments are also possible. For example, in some embodiments, the marking unit comprises a moveable tab configured to indicate a site corresponding to a center of a scan plane. The moveable tab can be configured, in certain embodiments, to make a visible indentation at a site corresponding to the center of the scan plane (which can correspond, for example, to the center of a cavity, hole, or other indicator formed in the marking unit). FIGS. 5A-5E is a set of schematic illustrations outlining the use of a moveable tab to indicate a target region. In FIG. 5A, tab 502 can be folded into a center cavity 408 within the marking unit 302 to make an indentation along target skin surface 412 at target insertion location 410 corresponding to the center of cavity 408. In FIG. 5A ultrasound transducer 108 is illustrated with an exemplary embodiment of the marking unit 302 comprising a cavity 408 and moveable tabs 502. Marking unit 302 can be attached to the hand grip region 120 of the ultrasound device 100 to cover transducer region 302. FIG. 5B illustrates ultrasound device 100 with marking unit 302 attached and pressed against the target skin surface 412 where ultrasound imaging can be conducted. As shown in FIG. 5C, a user's hand 404 can press against marking unit tab regions 420 in order to remove marking unit 302 from ultrasound device 100 while maintaining marking unit 302 along the target skin surface 412 at the target insertion location 410. As illustrated in FIG. 5D, marking unit 302 can be removed from imaging device 100. As shown in FIG. 5E, the user's hand 404 can activate moveable tabs 502, which can make an indentation along target skin surface 412 at the target insertion location 410. According to certain embodiments, a probe may then be inserted at the point at which the indentation has been made.

FIG. 6 is a schematic illustration showing an exemplary mechanical attachment scheme that can be used to connect a marking unit 302 with an imaging device 100. The marking unit 302 in FIG. 6 is configured to "self-attach" to the device housing 102. Self-attachment can be achieved by previously described means including, in one embodiment, a form fitting between the device housing 102 and marking unit 302 such that frictional forces are sufficient to ensure attachment. The wings 420 of the marking unit 302 in FIG. 6 can be advantageous, according to certain although not necessarily all embodiments, because it can improve one's ability to adhere the marking unit to a target skin surface. Additionally, wing regions can provide areas whereby a user can press against to detach the marking unit 302 from the device housing 102.

Figure 7:
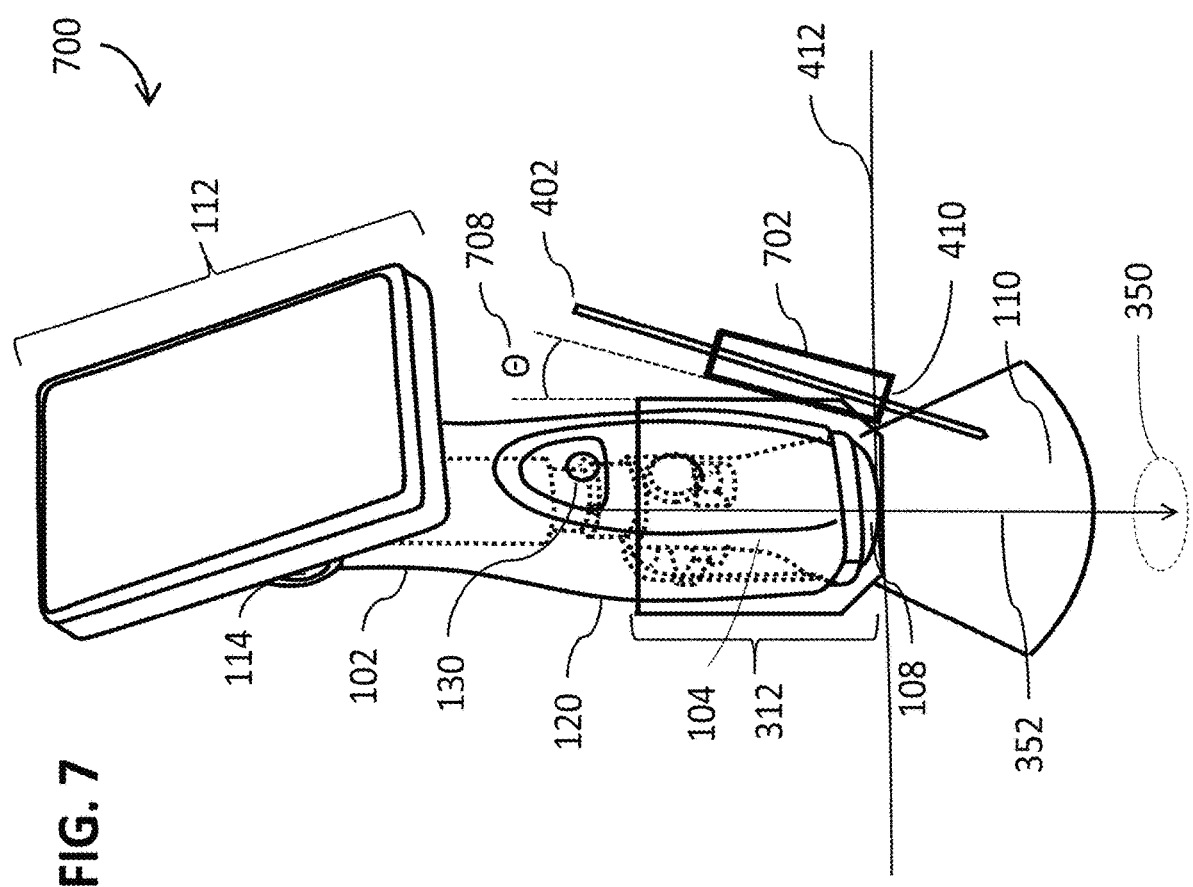
FIG. 7 is a schematic illustration of an exemplary detachable marking unit comprising a needle sleeve, according to certain embodiments.
Figure 8:
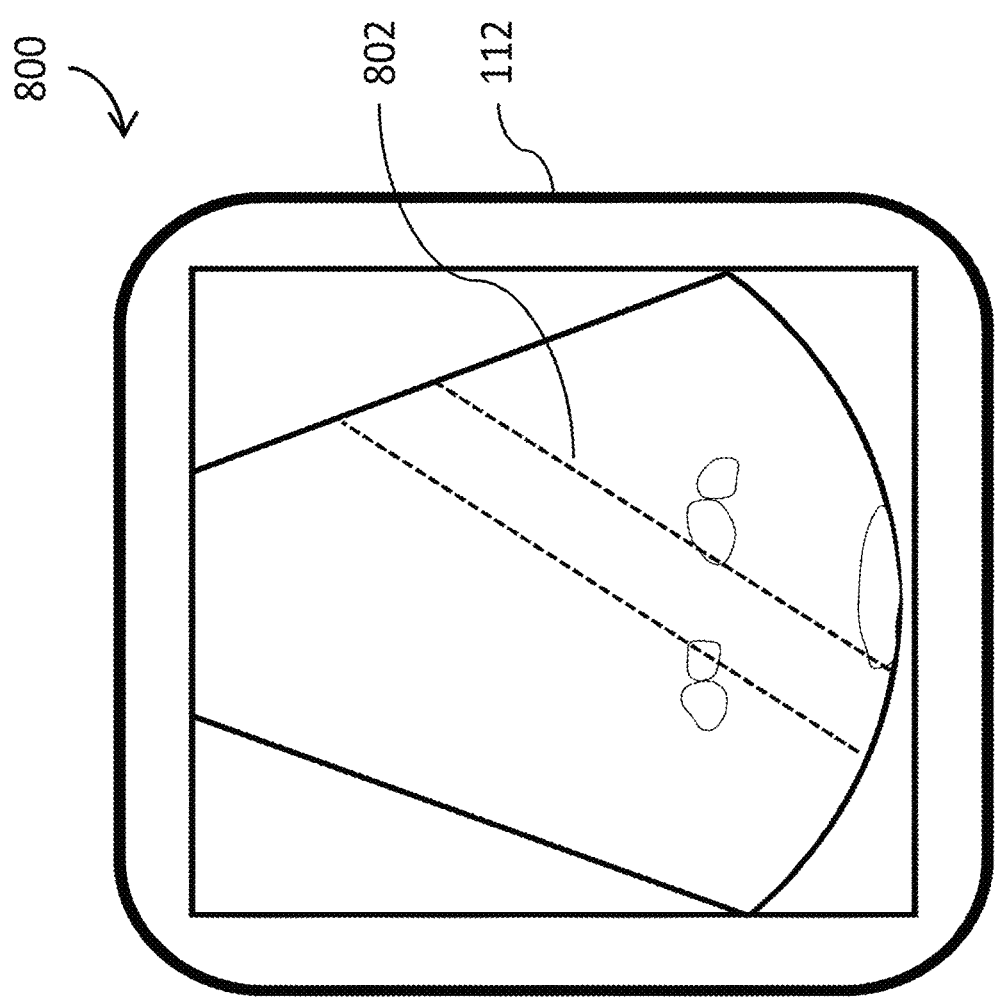
FIG. 8 is an exemplary imaging unit display, according to one set of embodiments.

In some embodiments, the marking unit 302 comprises a sleeve 702 comprising an elongated lumen passing through it. The sleeve can be used as a probe indicator, as described above. For example, the elongated lumen of the sleeve can be used to guide or otherwise house an elongated device such as a probe 402. FIG. 7 is a schematic illustration of one set of embodiments in which a cover 312 comprises a sleeve 702, which is being used to house a probe, such as a needle 402. The sleeve 702 can be configured to control the angle 708 of the elongated probe 402 that is threaded through the lumen (e.g., a needle 402 to be inserted at the target region 350). The imaging device display 112 can convey the angle 708 information with indicators such as, for example, dashed lines 802 superimposed on the ultrasound image. The user can then manually scan the imaging device 100 across the target skin surface 412 until the dashed line(s) 802 pass through the target of interest (e.g., blood vessel, nerve structure, epidural space) and then project the probe 402 through the sleeve 702. An example image display 112 in which overlaying indicator lines 802 are used to indicate the projected path of a probe 402 relative to the image if inserted through the sleeve 702 is illustrated in FIG. 8.

As noted above, certain aspects are related to configurations of a handheld ultrasound imaging device in which the target that is being imaged, the ultrasound imaging unit, and the marking unit are aligned during use. Alignment of these components during use can make location of target regions relatively easy for the user. According to certain embodiments, the marking unit is positioned such that, during use, a line extending between the target and the ultrasound imaging unit intersects the marking unit.

For example, referring to FIG. 3A, target region 350, marking unit 302, and imaging unit 104 are aligned such that line 352 (which extends infinitely, as indicated by the arrow at the ends of the line) intersects marking unit 302. It should be understood that a line is said to "intersect" a marking unit when the line passes through any region that lies within the outer geometric boundary of the marking unit, which includes both regions of the solid material that makes up the marking unit as well as voids (e.g., holes and the like) within such regions. As an illustrative example, FIG. 3B is a schematic cross-sectional schematic illustration of marking unit 302 shown in FIG. 3A. Marking unit 302 includes cavity 354 formed within a surrounding solid material 356, and defines outer geometric boundary 358. Although cavity 354 is not formed of any material per se, a line extending through cavity 354 would still be said to "intersect" marking unit 302.

Referring to FIGS. 4A-4C, marking unit 302, imaging unit 104, and target region 350 are also aligned such that line 352 intersects marking unit 302. In FIG. 5D, marking unit 302, imaging unit 104, and target region 350 are aligned such that line 352 intersects marking unit 302. In FIG. 7, imaging unit 104, and target region 350 are aligned such that line 352 intersects marking unit 302.

According to certain embodiments, the longitudinal axis of the housing intersects the marking unit (and, in some such embodiments, the longitudinal axis of the housing extends between the target and the ultrasound imaging unit). In some embodiments, the longitudinal axis of the hand grip region intersects the marking unit (and, in some such embodiments, the longitudinal axis of the hand grip region extends between the target and the ultrasound imaging unit).

According to certain embodiments, during use, the marking unit is positioned between the ultrasound imaging unit and the target that is to be imaged. For example, in FIG. 3A, marking unit 302 is positioned such that imaging unit 104 is above marking unit 302, and target region 350 is below marking unit 302. In other embodiments, the imaging unit could be located between the marking unit and the target region, for example, by sliding the marking unit up the hand grip region 120 of the housing.

In certain embodiments, a cover for an ultrasound imaging device is described. The cover comprises, in certain embodiments, a cover body configured to be attached to an imaging device, and a marking unit attached to the cover body and configured to indicate proper placement of a probe (e.g., a needle and/or a catheter) along a target that is to be imaged. Such imaging can allow a target anatomy to be reached with the probe, according to certain embodiments.

FIG. 3A is an exemplary schematic illustration of a cover 312 including a cover body 304 and detachable marking unit 302 connected to an imaging device 100. In FIG. 3A, the cover body covers the hand grip region 120 (e.g., including the imaging unit 104 and ultrasound transducer 108). The cover 312 can be used, in certain embodiments, as a sterile shield to the target skin surface 412 (e.g., the skin of a subject). According to certain embodiments, cover 312 can comprise an elastomeric band 306 and tab 308, for example, to facilitate the placement of cover 312 over hand grip region 120.

The cover body can be "self-attaching" to the imaging device, in certain embodiments. That is to say, in some embodiments, substantially no separate attaching material (such as a rubber band) is required to attach the cover body to the imaging device. Examples of mechanisms that can be used to attach the cover body to the imaging device in this way include, but are not limited to, a pair of magnets between the cover body and the hand grip region, mechanical attaching mechanisms (such as a fitted plastic inserts, spring-loaded retaining clips, elastic bands), and the like.

In certain embodiments, cover body 304 and/or marking unit 302 may be disposable. In some embodiments, cover body 304 and/or marking unit 302 may be sterile.

In certain embodiments in which a cover body is employed, the cover body and the marking unit can be removably attached to each other. For example, the cover body and the marking unit can be attached to each other, in certain embodiments, such that separation of the cover body and the marking unit does not damage either of the cover body and the marking unit. In some embodiments, the cover body and the marking unit can be attached to each other such that separation of the cover body and the marking unit can be achieved by hand, and does not require an additional tool (e.g., a screwdriver or other such tool). Examples of mechanisms that can be used to attach the marking unit to the imaging device (and/or the cover body, when employed) in this way include, but are not limited to, magnetic fittings (e.g., a pair of magnets between the housing and the marking unit), mechanical attaching mechanisms (such as a fitted plastic inserts, spring-loaded retaining clips, frictional fittings, elastic bands, hook and loop fasteners, screw threads), and the like.

In some embodiments, the marking unit is configured such that when it is attached to the imaging device, an image can be produced without the use of transmission medium. According to certain embodiments, when marking unit is attached to the imaging device, an image can be produced without substantial acoustic attenuation derived from the marking unit and without the use of transmission medium. For example, in some embodiments, less than 6 dB round-trip acoustic attenuation is observed at 1 MHz center frequency, without the use of transmission medium, when the marking unit is positioned as described elsewhere herein (e.g., when the marking unit is aligned with the ultrasound imaging unit and the target, as described elsewhere herein).

In some embodiments, the cover can be configured such that when it is attached to an ultrasound imaging device, received ultrasound data can be recorded for display of an image to the device display without the use of ultrasound gel or other ultrasound transmission medium being placed in between the transducer and the cover and/or marking unit. In contrast, other ultrasound imaging systems generally require the use of ultrasound gel to produce an image with acceptable image quality. The requirement for ultrasound transmission medium between the transducer and cover and/or marking unit can be eliminated, according to certain embodiments, by attaching the cover and/or marking unit to the transducer such that substantially no air is present between the two objects. For example, in some embodiments, an elastomeric band or other attaching mechanism can be configured such that the when the cover is attached to the ultrasound imaging device, it is pressed with high tension against the transducer surface. The tension can be made to be sufficiently high such that there substantially no air can be present between the two objects. In this way, the ultrasound beam can transmit between the two materials (i.e. transducer and cover) without requiring transmission medium. Exemplary materials from which the marking unit can be made include, for example, polyurethane, polyethylene, and silicone.

In some embodiments in which a cover body is employed (in addition to the marking unit), the cover is configured such that when it is attached to the imaging device, an image can be produced without substantial acoustic attenuation derived from the cover and without the use of transmission medium. For example, the cover can be configured, in certain embodiments, such that when it is attached to an ultrasound imaging device, received ultrasound data can be recorded for display of an image to the device display without the use of ultrasound gel or other ultrasound transmission medium being placed in between the transducer and the cover. The cover can be configured for us without transmission medium, for example, by using a cover material that is thin (e.g., less than about 5 mm thick) and/or by employing a self-attaching mechanism that holds the cover material against the transducer face with sufficient strength during operation of the imaging device. In this way, substantially no air is trapped between the cover and transducer face, and the cover itself is too thin to cause appreciable attenuation or reflections that can lead to unacceptable image quality (e.g., less than 6 dB round-trip acoustic attenuation at 1 MHz center frequency). Example cover materials can include, for example, polyurethane, polyethylene, and silicone.

As noted above, the ultrasound imaging devices described herein can produce ultrasound images using a variety of known techniques. In certain embodiments the ultrasound transducer (e.g., ultrasound transducer 108) can include a mechanically scanned single element transducer. In some embodiments, the ultrasound transducer can be a linear array, a two-dimensional array, or an annular array. In certain embodiments the ultrasound imaging unit (e.g., ultrasound imaging unit 104) can be configured to produce, for example, a B-mode image, a C-mode image, an M-mode image, a tissue harmonic image, a three-dimensional image, a Color Doppler image, a Power Doppler image, a Pulse-wave Doppler image, a continuous wave Doppler image, an ultrasound contrast agent enhanced image, a B-flow image, or any other mode or combination of modes whereby an image is formed from information received by the ultrasound transducer. Those of ordinary skill in the art of ultrasound understand that an ultrasound imaging unit generally comprises a combination of one or more of an ultrasound transducer, and circuitry and processing units for conditioning, processing, and transferring image data to the display unit. The ultrasound imaging unit can be contained within the device housing. For example, in some embodiments, the ultrasound-imaging unit can comprise an ultrasound transducer, an ultrasonic signal conditioning circuit, and a processor circuit, which can be communicatively connected via a bus. The ultrasonic signal conditioning circuit can include a number of conventional processing circuitries such as beam-forming circuitry or other processing circuitry. For example, the ultrasonic signal conditioning circuit can be configured to amplify, phase-shift, time-gate, filter, or otherwise condition received ultrasonic information (e.g., echo information), such as provided to the processor circuit. In a further example, the receive path from each transducer element can include one or more of a low noise amplifier, a main-stage amplifier, a band-pass or a low-pass filter, or an analog-to-digital converter. In one example, one or more signal conditioning steps can be performed digitally, such as by using the processor circuit. The term processor is used to generically refer to digital circuitry that can be used to manipulate ultrasound information obtained from the ultrasound transducer. Such circuitry can include one or more of a field-programmable gate array (FPGA) or other programmable logic devices (PLDs), microprocessor, a system-on-chip including one or more execution cores or other circuitry, a microcontroller, or one or more or other circuits. Those of ordinary skill in the art of ultrasound and image processing will understand that the signal conditioning and processing steps and their order of operation to be performed by the signal conditional circuit and processor circuit will vary depending on the desired image to be rendered to the display (e.g., B-mode image, C-mode image, M-mode image, tissue harmonic image, three-dimensional image, Color Doppler image, Power Doppler image, Pulse-wave Doppler image, continuous wave Doppler image, ultrasound contrast agent enhanced image, or B-flow image).

In some embodiments of the handheld ultrasound imaging device disclosed herein, the ultrasound images on the display can be rotated or flipped to different orientations depending on the position of the display screen, or in response to user input, in order to make the images more useful to the user. Rotating or flipping the ultrasound images can make the images more useful to the user by ensuring that the images are oriented similarly to the underlying structures in the body of the subject being imaged.

Referring to FIGS. 9A-9E, an embodiment of a handheld ultrasound imaging device with a rotatable display screen can be seen in side view, with the screen in different rotational positions. Display screen 112 of imaging device 900 is attached to housing 120 via pivot 114, which allows the screen to be rotated about axis 116. Display screen 112 is oriented at angle 910 with respect to longitudinal axis 106 of housing 112, with angle 910 ranging from 0 degrees in FIG. 9A to 180 degrees in FIG. 9E, with FIGS. 9B, 9C and 9D showing positions in between these extremes. Once the display screen is rotated into a given position by a user, it is held in such position by a mechanism within the pivot, without the need for the user to hold the display screen in such position. Any suitable mechanism may be used for this purpose, such as magnets, detents, friction fittings, or other mechanisms known in the art. The positions shown in FIGS. 9A-9E are not meant to be limiting, and in some embodiments the display screen may be capable of being held in positions other than those shown, or in a greater number of positions than those shown, or to be continuously adjustable between the extreme positions shown in FIGS. 9A and 9E.

In some embodiments the display screen may be capable of being rotated through a range of angles greater than 180 degrees. In some embodiments the display screen may be capable of being rotated about one or more axes other than axis 116, in addition to or in place of axis 116.

The image flip feature is illustrated in FIGS. 10A-10B and 11A-11C. FIGS. 10A and 10B show an exemplary handheld ultrasound imaging device 1000, in side and front view respectively. Rotatable display screen 112 is in the 0 degree position, corresponding to the position shown in FIG. 9A. FIG. 10B shows the device 1000 of FIG. 10A as viewed from the left-hand side. Device 1000 is performing ultrasound scanning along scanning plane 110. Ultrasound transducer 1008 is held against skin surface 1020. Probe 1030, such as a needle, catheter, or other device, is partially under skin surface 1020, and is being directed by a surgeon, technician or other professional toward target 1040, such as a lesion blood vessel, nerve, or other anatomical feature; alternatively, target 1040 may be an anatomical feature to be avoided by the probe. Probe 1030 and target 1040 are used for illustrative purposes, to illustrate the image rotation and flip features disclosed herein, and are not meant to be limiting as to the types of images to which the device or the feature applies. Display screen 112 shows ultrasound images of the probe 1030' and the target 1040', which images are used to help direct the probe 1030 toward or away from the target 1040. The images 1030' and 1040' are oriented similarly the orientation of probe 1030 and target 1040, from the perspective of a user facing the display screen 112, helping make such images be useful to the user who is directing the probe. Screen feature 1015 appears above display screen 112, indicating to a user that the display screen is in a right-side-up orientation, as it would appear when the display screen is at the 0 degrees rotational position, also called "compact orientation," as shown in FIG. 10A. According to various embodiments screen feature 1015 may comprise a label, or one or more electronic indicators, e.g. LEDs, showing information relevant to the status or functioning of the device, or other features.

FIGS. 11A-11C show the same handheld ultrasound imaging device 1000 as in FIGS. 10A-10B, with the display screen 112 rotated 180 degrees, also called "extended orientation," corresponding to the position shown in FIG. 9E. FIG. 11A shows the device is side view, and FIGS. 11B-11C show the device in rear view, i.e. looking at device in FIG. 11A from the right-hand side. Because the display screen 112 has been rotated 180 degrees, the screen now appears upside-down, with screen feature 1015 appearing at the bottom. As in FIGS. 10A-B, the device is being used to acquire and display ultrasound images of a probe 1030 and a target 1040 lying under skin surface 1020.

In FIG. 11B, the images 1030' and 1040' appear on the screen as they do in FIG. 10B. However, because the display screen 112 has been rotated, the images have been inverted, and the image 1030' of the probe 1030 now appears above the image 1040' of the target 1040, contrary to the positions of the probe 1030 and target 1040 from the perspective of a user looking at the display screen 112. Consequently, the images 1030' and 1040' may be more difficult to use in guiding probe 1030 to or away from target 1040. In FIG. 11C, by contrast, the images on display screen 112 have been vertically flipped, so that they form a mirror image of the images as they appear on display screen 112 in FIG. 11B. As a consequence of the images being flipped, images 1030" of the probe and 1040" of the target now appear "right-side up," i.e. in orientations that correspond to the orientations of probe 1030 and target 1040 under skin surface 1020, from the perspective of a user looking at the display screen 112. Consequently, such images 1030" and 1040" may be easier to use in helping to accurately guide probe 1030 with respect to target 1040. An image orientation wherein the image features and the actual structures in the body have the same orientation may provide a more intuitive view to a user of the images, thus increasing ease of use and accuracy in performing procedures guided by ultrasound images.

A user of the device may find it convenient or necessary, while performing a procedure guided by ultrasound images, to position himself in a variety of positions vis-à-vis the site being imaged, and consequently to adjust the position of the rotatable display screen so as to be able to best view the images. The ability to adjust the rotational position of the display screen allows the ultrasound imaging device and probe to be held at different orientations while still maintaining good visibility of the screen. Having a display screen co-located with the ultrasound probe, as in the handheld ultrasound imaging device disclosed herein, makes it easier to perform procedures guided by ultrasound images because the display screen, ultrasound probe, needle/catheter/etc. and hand are all in the same line of sight. With the image flip feature, the images on the screen are displayed in an orientation that is most useful to the user in guiding the procedure, thus allowing the user to take fullest advantage of the compactness of the device. In some embodiments, the ultrasound imaging device comprises one or more sensors that senses the rotational position of the display screen, and a processor that receives input from the sensor or sensors. The processor, which is in electronic communication with both the sensor(s) and the display screen, sends a signal to the display screen instructing that the ultrasound images be flipped, or not flipped, depending on the position of the screen. In some embodiments a position sensor comprises an accelerometer or similar device that detects the orientation of the display screen with respect to the direction of gravity, i.e. which end of the screen is "up." In some embodiments the pivot mechanism by which the rotatable display screen rotates comprises one or more electronic switches that sense the position of the display screen with respect to part of the housing to which the display screen is attached, and thus act as a rotational position sensor. Such switches may include a limit switch that detects when the display has rotated past the 90-degree position shown in FIG. 9C. In some embodiments the orientation in which the ultrasound images are displayed may be determined based in part on a rotational position of the display screen with respect to the scanning plane, as determined by the sensors and the processor.

The image rotation feature is illustrated in FIGS. 12A-C. FIG. 12A shows in side view an exemplary handheld ultrasound imaging device 1000, with display screen in the 90-degree or horizontal position, corresponding to the position shown in FIG. 9C. The device is shown in top view in FIGS. 12B and 12C, where only the display screen 112 can be seen. The device is acquiring ultrasound images along imaging plane 110, with the images 1210, including images of probe 1230 and target 1240, displayed on display screen 112. The "top" of display screen 112, as indicated by screen feature 1015, appears on the right-hand side in FIGS. 12B-12C; in "compact orientation" or 0-degree rotational position, the top of display screen 112 is actually at the top, as in FIG. 10B. In FIG. 12B the images are displayed in their standard orientation, in this case with the image of target 1240 appearing nearer to the "top" of display screen 112, as indicated by screen feature 1015, and the image of probe 1230 extends away from the image of target 1240 toward the lower-right corner 1250 of display screen 112. In FIG. 12C the images 1210 have been rotated 90 degrees clockwise, such that the image of target 1240' now appears closer to right-hand side 1270 of display screen 112, and image of probe 1230' now extends toward lower-left corner 1260 of display screen 112.

Rotating the images on the display screen, as in FIG. 12C, may be helpful to a user of the ultrasound images by making the orientation of the images correspond more closely to the orientation of the anatomical structures being imaged. This may help a user in visualizing such structures, and may be useful in performing procedures guided by ultrasound. The 90-degree clockwise rotation shown in FIG. 12C is illustrative; images could also be rotated counter-clockwise, or by 180 degrees, or by angles other than 90 or 180 degrees, according to various embodiments.

In some embodiments, the ultrasound imaging device comprises one or more sensors that senses the rotational position of the display screen, and a processor that receives input from the sensor or sensors. The processor, which is in electronic communication with both the sensor(s) and the display screen, sends a signal to the display screen instructing that the ultrasound images be rotated, and by how much and in which direction, or not rotated, depending on the position of the screen. In some embodiments a position sensor comprises an accelerometer or similar device that detects the orientation of the display screen with respect to the direction of gravity, i.e. which end of the screen is "up," or whether the screen is in a horizontal or near-horizontal orientation as in FIG. 12A. In some embodiments the pivot mechanism by which the rotatable display screen rotates comprises one or more electronic switches that sense the position of the display screen with respect to part of the housing to which the display screen is attached, and thus act as a rotational position sensor. In some embodiments the orientation in which the ultrasound images are displayed may be determined based in part on a rotational position of the display screen with respect to the scanning plane, as determined by the sensors and the processor.

In some embodiments the handheld ultrasound imaging device may be configured to flip and/or rotate ultrasound images as shown on a display screen in response to user input or commands. According to various embodiments such user input can comprise the use of buttons or other actuators that are integral to or attached to the device. Such user input can comprise the use of one or more screen gestures on a touch-sensitive display screen that is used to display the images; for example, a circular swipe gesture could be used to rotate an image. Such user input can also comprise voice commands, which would allow a user to change the display orientation without taking his or her hands away from their other tasks, such as performing a procedure guided by the ultrasound images. Such user input can also comprise instructions issued using a device separate from the ultrasound imaging device, for example a mobile phone, and transmitted to the ultrasound imaging device via wireless or wired means. According to various embodiments, any or all of the foregoing types of user input may be enabled for the purposes of changing the orientation of ultrasound images on the display screen. According to some embodiments, the ultrasound imaging device may combine the automatic flipping and/or rotation of ultrasound images in response to position sensor input with the flipping and/or rotation of ultrasound images in response to user input and commands. For example, user input could have the effect of overriding an image orientation that is put into effect automatically as a result of input from the position sensor or sensors.

Figure 13:
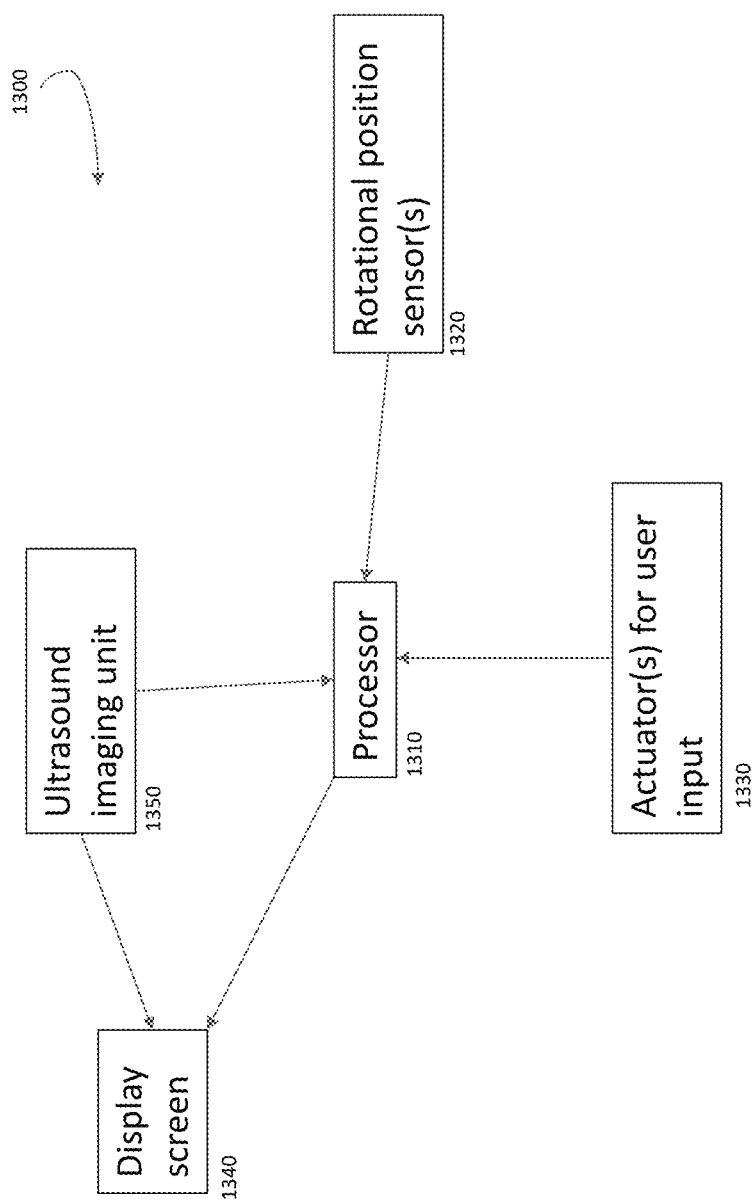
FIG. 13 is a schematic illustration of an exemplary system architecture for a handheld ultrasound imaging device with an image flip and rotation feature as disclosed herein, according to one or more embodiments.

An exemplary internal architecture 1300 of a handheld ultrasound device with the image rotation and flipping feature is shown schematically in FIG. 13. Processor 1310 is in communication with rotational position sensor(s) 1320, and continuously receives information regarding rotational position of the display screen. Processor 1310 is also in communication with user input actuator(s) 1330, and receives information regarding commands issued by the user. Based on sensor input and user input, processor 1310 determines the proper orientation of the ultrasound images on display screen 1340, and transmits signals to display screen 1340 to display the ultrasound images received from ultrasound imaging unit 1350 according to such orientation.

Figure 14:
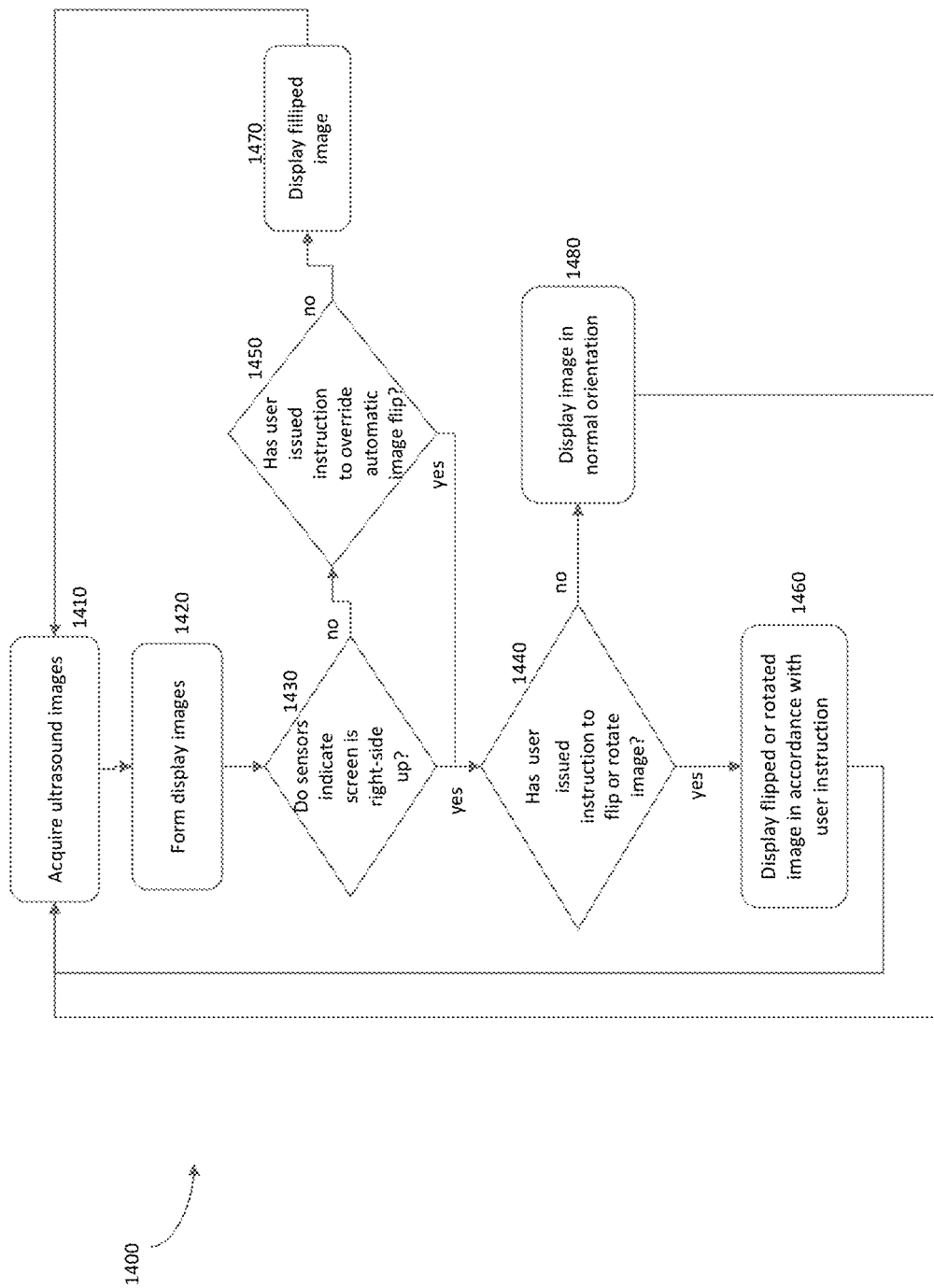
FIG. 14 is an exemplary flowchart for procedures followed by a processor in implementing the ultrasound image flip and rotation features in a handheld ultrasound imaging device as disclosed herein, according to one or more embodiments.

An exemplary procedure for flipping and/or rotating the ultrasound images shown on the handheld ultrasound imaging device disclosed herein is illustrated in flowchart 1400 in FIG. 14. The device acquires ultrasound images at step 1410, and forms the ultrasound images into screen images at step 1420. At step 1430 the processor determines, based on input from the position sensor(s) determine whether the display screen is in a right-side-up orientation. If the answer is yes, or if automatic screen flip is not enabled, then the step 1440 is reached, at which the processor determines if the user has issued an instruction to flip or rotate the images on the display screen. If the answer is yes, then at step 1460 the images are displayed on the screen in flipped or rotated orientation, in accordance with the user instruction received. If the answer is no, then at step 1480 the images are displayed in normal orientation; that is, neither flipped nor rotated.

If at step 1430 it is determined that the screen is not in right-side-up orientation, then the procedure goes to step 1450, at which the processor determines whether the user has issued an instruction that overrides automatic image reorientation. If the answer is no, then at step 1470 the ultrasound images are displayed in flipped orientation. If the answer is yes, then the procedure goes to step 1440, where it is determined what image orientation the user has instructed, and the images are displayed accordingly at either step 1460 or step 1480. From steps 1460, 1470 and 1480, the procedure returns to step 1410 where the device acquires further images, and the procedure repeats.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A handheld ultrasound imaging device, comprising:
a housing comprising:
an ultrasound imaging unit;
a hand grip region disposed on the housing between a rotatable display and the ultrasound imaging unit; and
a processor capable of processing received ultrasound image data and forming an ultrasound image, including an image of a probe advanced or being used by a user of the handheld ultrasound imaging device,
wherein the rotatable display is configured to receive and display the ultrasound image formed by the processor,
wherein the rotatable display is configured to be rotated, relative to at least another portion of the housing, about at least one rotational axis by at least 30 degrees,
wherein the housing is capable of being operated at any orientation relative to a direction of gravity,
wherein the rotatable display is capable of displaying the ultrasound image, the ultrasound image data, or combinations thereof, in a plurality of image orientations,
wherein the plurality of image orientations allows the user of the handheld ultrasound imaging device to view an orientation of the probe that substantially matches the actual orientation of the probe being used in or on a subject from a perspective of the user, and
wherein the handheld ultrasound imaging device is capable of allowing the user to move relative to the subject while rotating the rotatable display and continuing to view an orientation of the probe on the rotatable display that substantially matches the actual orientation of the probe being used in or on the subject.

2. The imaging device of claim 1, further comprising a sensor capable of sensing a rotational position of the rotatable display.

3. The imaging device of claim 2, wherein the rotational position is relative to a direction of gravitational pull.

4. The imaging device of claim 2, wherein the rotational position is relative to another portion of the housing.

5. The imaging device of claim 2, wherein the rotational position is relative to a scanning plane of the ultrasound imaging unit.

6. The imaging device of claim 2, wherein the sensor comprises an accelerometer.

7. The imaging device of claim 2, wherein the sensor comprises an electronic switch connected to a portion of the housing about which the rotatable display is configured to be rotated.

8. The imaging device of claim 2, wherein the rotatable display is configured to display the ultrasound image in an image orientation determined at least in part by an input received from the sensor.

9. The imaging device of claim 1, wherein the rotatable display is configured to display the ultrasound image in an image orientation determined at least in part by an input received from the user of the ultrasound imaging device.

10. The imaging device of claim 1, wherein the rotatable display comprises a touch-sensitive screen.

11. The imaging device of claim 1, wherein the imaging device further comprises a microphone capable of detecting a voice command spoken by the user.

12. The imaging device of claim 1, wherein the plurality of image orientations comprise a first image orientation and a second image orientation, the second image orientation comprising a mirror image of the first image orientation.

13. The imaging device of claim 12, wherein the plurality of image orientations further comprise a third image orientation, the third image orientation comprising a 90-degree rotation of the first image orientation.

14. The imaging device of claim 12, wherein the rotatable display is configured to display the ultrasound image in a display orientation, the display orientation comprising either the first image orientation or the second image orientation, and wherein the display orientation is determined by an image flip condition.

15. The imaging device of claim 14, further comprising a sensor capable of sensing a rotational position of the rotatable display, wherein the processor is in electrical communication with each of the sensor and the rotatable display, wherein the processor is configured to determine the image flip condition based at least in part on input received from the sensor.

16. The imaging device of claim 15, wherein the processor is configured to transmit an electronic signal to the rotatable display, said electronic signal instructing the rotatable display to display the ultrasound image in either the first image orientation or the second image orientation, depending on the image flip condition.

17. The imaging device of claim 14, wherein the processor is in electrical communication with the rotatable display, wherein the processor is configured to determine the image flip condition based at least in part on an input received from the user of the ultrasound imaging device.

18. The imaging device of claim 17, wherein the processor is configured to transmit an electronic signal to the rotatable display, said electronic signal instructing the rotatable display to display the ultrasound image in either the first image orientation or the second image orientation, depending on the image flip condition.

19. The imaging device of claim 1, wherein the housing is elongated and comprises a longitudinal axis.

20. The imaging device of claim 19, wherein a smallest angle between a scanning plane of the ultrasound imaging unit and the longitudinal axis of the housing is less than 45 degrees.

21. The imaging device of claim 19, wherein a scanning plane of the ultrasound imaging unit is substantially parallel to the longitudinal axis of the housing.

22. The imaging device of claim 1, wherein the rotatable display is configured to be rotated such that the rotatable display can be oriented in a first position substantially parallel to a scanning plane of the ultrasound imaging unit and in a second position substantially perpendicular to the scanning plane of the ultrasound imaging unit.

23. The imaging device of claim 1, further comprising a cover body attached to the housing.

24. The imaging device of claim 23, wherein a marking unit is detachably coupled to the cover body.

25. The imaging device of claim 23, wherein the cover body is configured such that when it is attached to the imaging device, the ultrasound image can be produced without the use of transmission medium.

* * * * *